(12) United States Patent
Makower et al.

(10) Patent No.: US 7,056,325 B1
(45) Date of Patent: Jun. 6, 2006

(54) TRANSLUMINAL METHODS AND DEVICES FOR CLOSING, FORMING ATTACHMENTS TO, AND/OR FORMING ANASTOMOTIC JUNCTIONS IN, LUMINAL ANATOMICAL STRUCTURES

(75) Inventors: Joshua Makower, Los Altos, CA (US); J. Christopher Flaherty, Los Altos, CA (US); Timothy R. Machold, Moss Beach, CA (US); John Thomas Garibotto, Newark, CA (US); Jason Brian Whitt, San Fransisco, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 405 days.

(21) Appl. No.: 10/259,210

(22) Filed: Sep. 27, 2002

Related U.S. Application Data

(62) Division of application No. 09/908,337, filed on Jul. 18, 2001, now Pat. No. 6,491,707, which is a division of application No. 09/543,251, filed on Apr. 5, 2000, now Pat. No. 6,287,317, which is a division of application No. 08/896,307, filed on Jun. 28, 1997, now Pat. No. 6,071,292.

(51) Int. Cl.
*A61B 17/04* (2006.01)
(52) U.S. Cl. .................. 606/153; 606/154; 606/157
(58) Field of Classification Search .............. 606/153, 606/154, 157
See application file for complete search history.

(56) References Cited

U.S. PATENT DOCUMENTS

| | | | | |
|---|---|---|---|---|
| 3,875,648 A * | 4/1975 | Bone | ............................ | 29/417 |
| 4,006,747 A * | 2/1977 | Kronenthal et al. | ........ | 606/144 |
| 4,235,238 A * | 11/1980 | Ogiu et al. | ................. | 606/145 |
| 4,512,338 A * | 4/1985 | Balko et al. | ................ | 128/1 R |
| 4,669,473 A * | 6/1987 | Richards et al. | ............ | 606/215 |
| 4,696,300 A * | 9/1987 | Anderson | .................... | 606/219 |
| 4,705,040 A * | 11/1987 | Mueller et al. | ............. | 606/108 |
| 5,342,393 A * | 8/1994 | Stack | ......................... | 606/213 |
| 5,470,337 A * | 11/1995 | Moss | ........................ | 606/139 |
| 5,645,551 A | 7/1997 | Green et al. | ................. | 606/143 |
| 5,653,744 A | 8/1997 | Khouri | .......................... | 623/1 |
| 5,695,504 A | 12/1997 | Gifford, III et al. | ........ | 606/153 |
| 5,709,335 A | 1/1998 | Heck | ........................ | 227/176.1 |
| 5,713,908 A | 2/1998 | Jameel et al. | ............... | 606/148 |
| 5,732,872 A | 3/1998 | Bolduc et al. | ............ | 227/176.1 |
| 5,782,844 A | 7/1998 | Yoon et al. | .................. | 606/139 |
| 5,797,930 A | 8/1998 | Ovil | ............................ | 606/148 |
| 5,810,850 A | 9/1998 | Hathaway et al. | ........... | 606/144 |
| 5,810,851 A * | 9/1998 | Yoon | .......................... | 606/148 |
| 5,810,882 A * | 9/1998 | Bolduc | ......................... | 606/213 |
| 6,319,263 B1 * | 11/2001 | Levinson | .................... | 606/144 |
| 6,626,919 B1 * | 9/2003 | Swanstrom | .................. | 606/153 |

FOREIGN PATENT DOCUMENTS

CA     2182070     2/1997

(Continued)

*Primary Examiner*—Gary Jackson

(57) ABSTRACT

Methods and apparatus for passing attachment apparatus (e.g., connector devices, staples, etc.) or connector material (e.g., suture thread, wire, cord, filament, monofilament, etc.) into or through the wall of a luminal anatomical structure (e.g., a blood vessel or other anatomical conduit) for the purpose of; i) closing the lumen of the anatomical structure, ii) forming an anastomotic junction between separate anatomical structures (or between approximated segments of the same anatomical structure), and/or iii) attaching an article (e.g., an endoluminal, extraluminal or transluminal graft) or other apparatus to the wall of the anatomical structure.

9 Claims, 16 Drawing Sheets

FOREIGN PATENT DOCUMENTS

| | | |
|---|---|---|
| WO | 9633673 | 10/1996 |
| WO | WO96/40356 | 12/1996 |
| WO | 9728745 | 8/1997 |
| WO | 9838941 | 9/1998 |
| WO | 9838942 | 9/1998 |
| WO | 9842262 | 10/1998 |

* cited by examiner

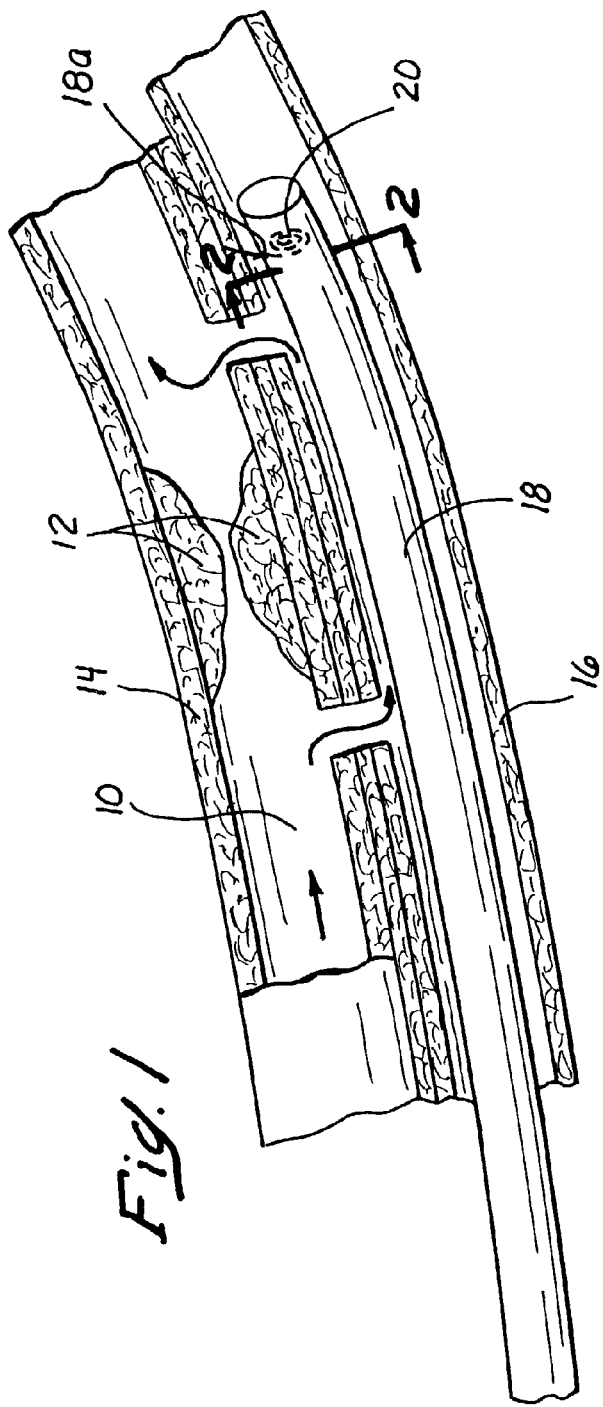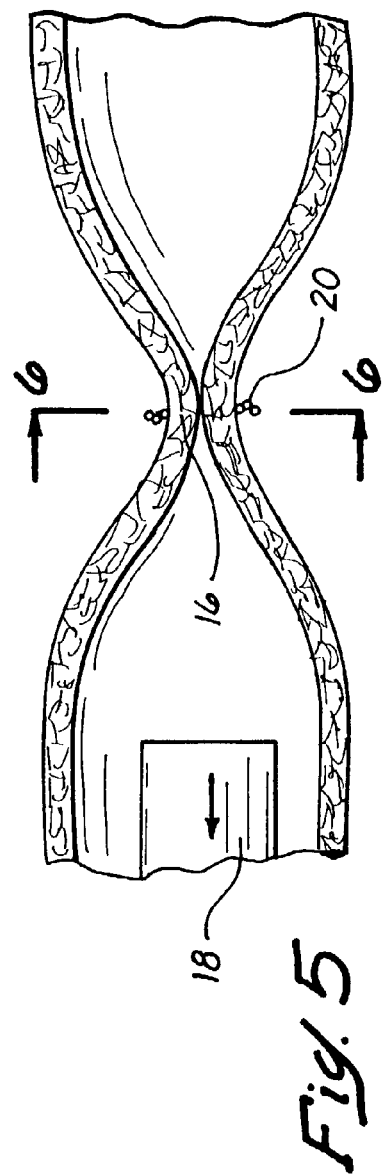

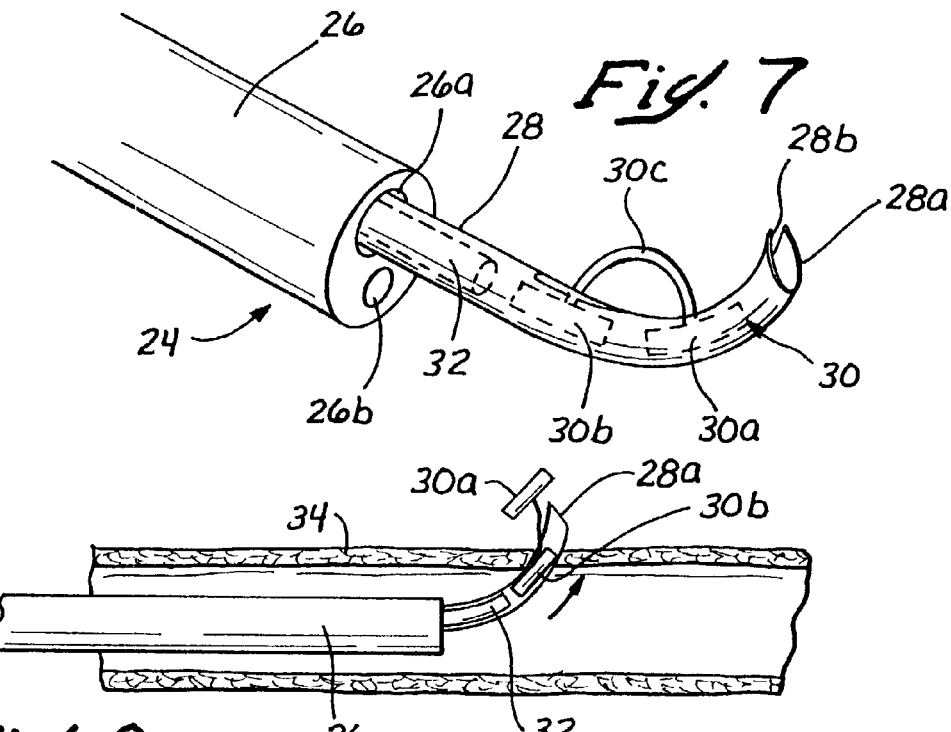
Fig. 7
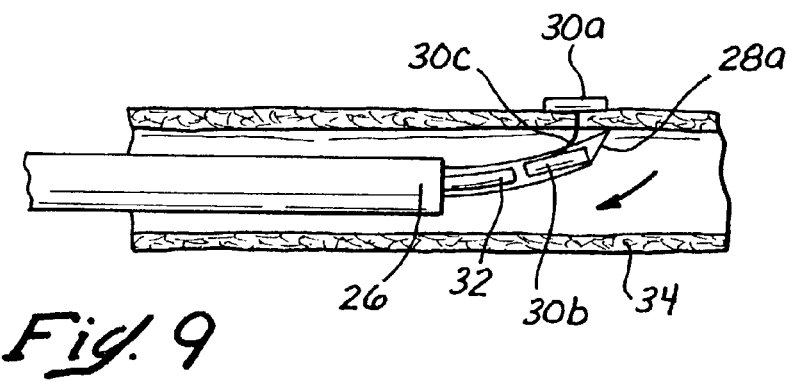
Fig. 8
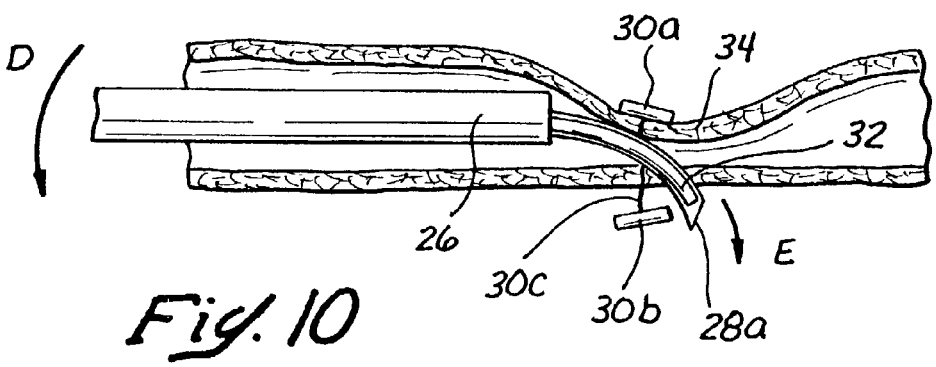
Fig. 9
Fig. 10

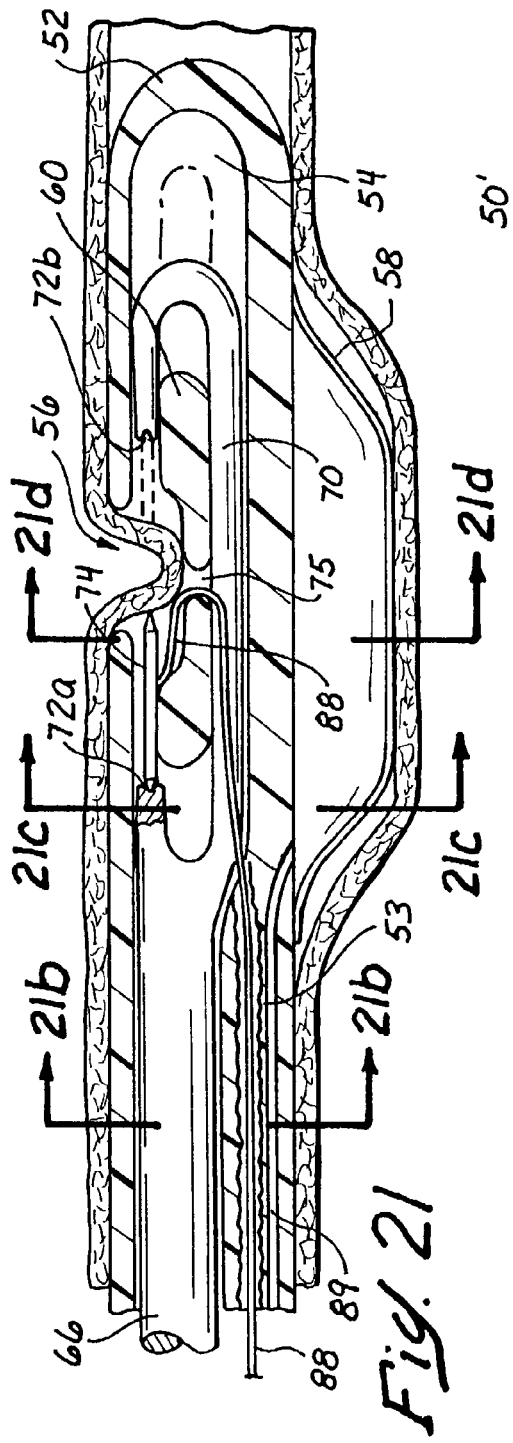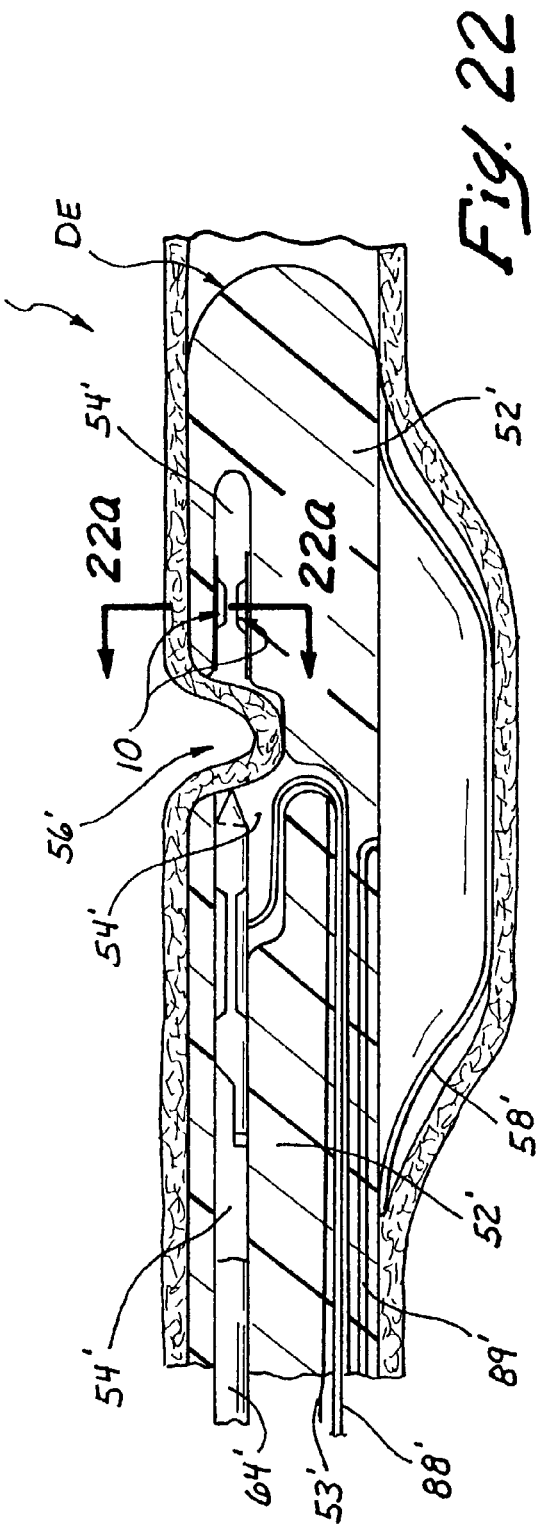

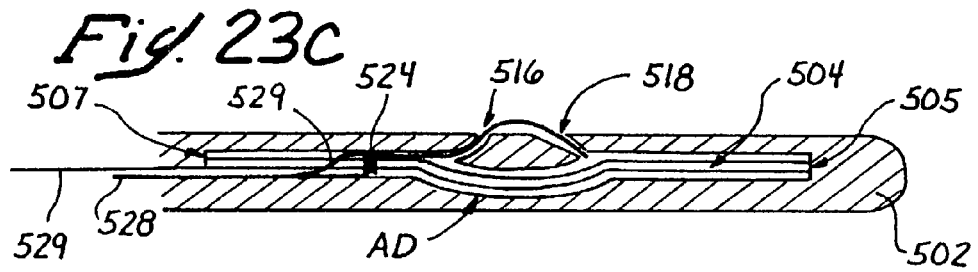
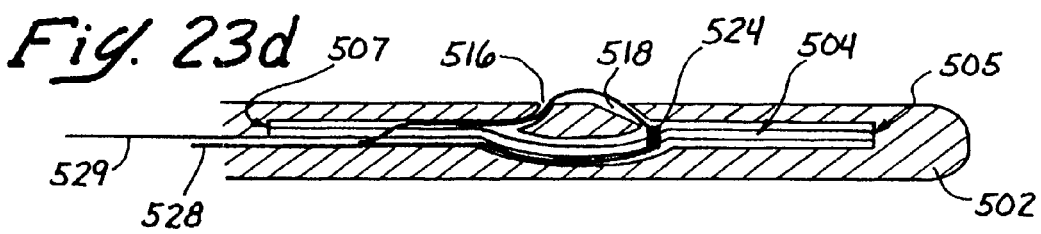
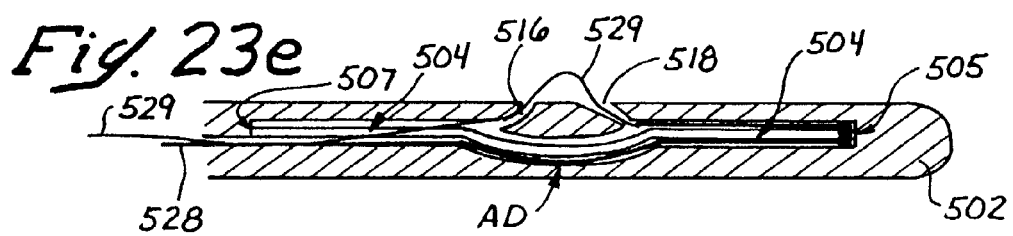
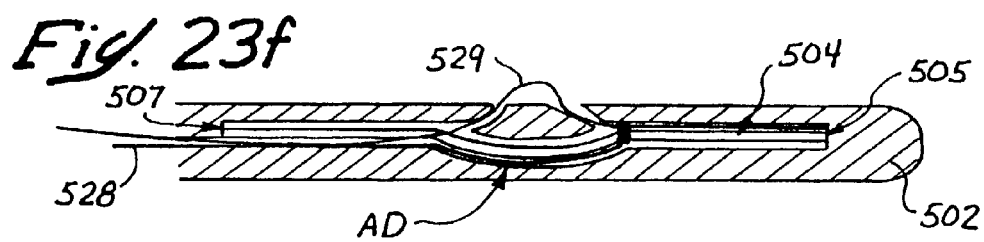
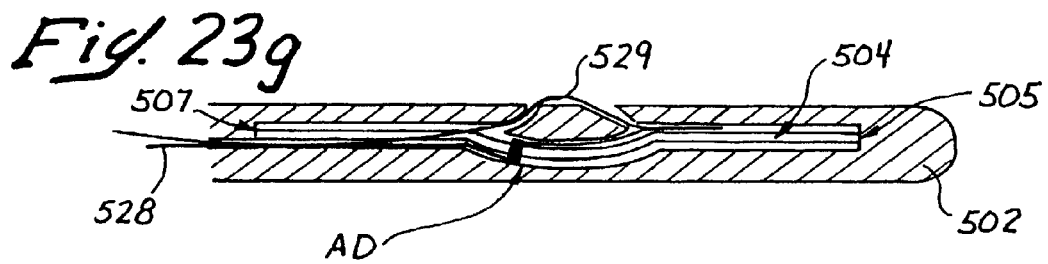
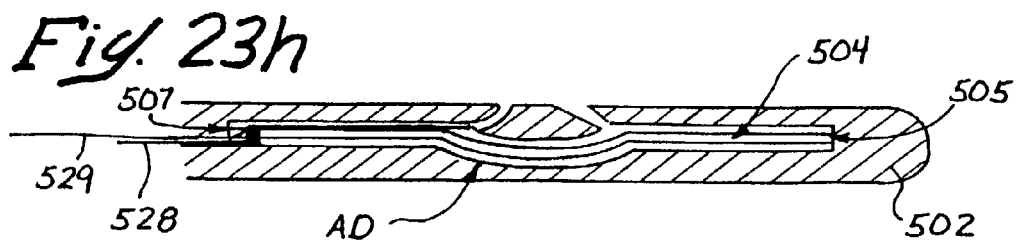

TRANSLUMINAL METHODS AND DEVICES FOR CLOSING, FORMING ATTACHMENTS TO, AND/OR FORMING ANASTOMOTIC JUNCTIONS IN, LUMINAL ANATOMICAL STRUCTURES

This is a divisional of application Ser. No. 09/908,337 filed on Jul. 18, 2001 now U.S. Pat. No. 6,491,707 which is a divisional of application Ser. No. 09/543,251 filed on Apr. 5, 2000 now U.S. Pat. No. 6,287,317, which is a division of Ser. No. 08/896,307 filed on Jun. 28, 1997 issued U.S. Pat. No. 6,071,292 filed on Jun. 28, 1977 issued on Jun. 6, 2000.

FIELD OF THE INVENTION

The present invention relates generally to medical devices and methods, and more particularly to intraluminal devices and methods for passing attachment apparatus (e.g., connector devices, staples, etc.) or connector material (e.g., suture thread, wire, cord, filament, monofilament, etc.) into or through the wall of a luminal anatomical structure (e.g., a blood vessel or other anatomical conduit) for the purpose of; i) closing the lumen of the anatomical structure, ii) forming an anastomotic junction between separate anatomical structures (or between approximated segments of the same anatomical structure), and/or iii) attaching an article (e.g., an endoluminal, extraluminal or transluminal graft) or other apparatus to the wall of the anatomical structure.

BACKGROUND OF THE INVENTION

In modern medical practice, it is sometimes desirable to pass attachment apparatus (e.g., connector devices, staples, etc.) or connector material (e.g., suture thread, wire, cord, filament, monofilament, etc.) into or through the wall of a luminal anatomical structure (e.g., a blood vessel or other anatomical conduit) for the purpose of; i) closing the lumen of the anatomical structure, ii) forming an anastomotic junction between separate anatomical structures (or between approximated segments of the same anatomical structure), and/or iii) attaching an article (e.g., an endoluminal, extraluminal or transluminal graft) or other apparatus to the wall of the anatomical structure. Some of these types of medical procedures are summarized as follows:

i. Procedures for Fully or Partially Closing of the Lumen of a Tubular Anatomical Structure Such As a Blood Vessel Examples of medical procedures wherein it is desirable to close the lumen of a blood vessel include: a) procedures intended to diminish or block the flow of blood into vascular aneurysms (e.g., cerebral aneurysms); b) procedures intended to occlude the side branches which emanate from a segment of a peripheral vein (e.g., to prepare the vein segment for use as an in situ bypass conduit); c) procedures intended to occlude varicose veins; d) transvascular, catheter-based procedures for bypassing obstructed, diseased or injured arteries as described in U.S. patent application Ser. Nos. 08/730,327 and 08/730,496; e) procedures intended to block or diminish blood flow to a tumor; f) procedures intended to close congenital or acquired arteriovenous malformations; g) procedures intended to temporarily or permanently block blood flow through a vessel as an adjuvant to placement of an implant or apparatus within the blood vessel (e.g., placement of an endovascular graft for treatment of an aneurysm or other therapeutic intervention); and procedures intended to close an interstitial puncture tract or fistula which has been created for use in performing another medical procedure. Included among the catheter-based arterial bypass procedures described in co-pending application Ser. Nos. 08/730,327 and 08/730,496 is a coronary artery bypass procedure wherein a passageway-forming catheter is transluminally advanced into the coronary vasculature, and a tissue-penetrating element is passed out of the catheter and through the wall of the vessel in which the catheter is positioned to create at least one blood flow passageway (e.g., a puncture tract or interstitial tunnel) between an obstructed coronary artery and an adjacent coronary vein. Arterial blood then flows from the obstructed coronary artery into the adjacent coronary vein. In one variation of the procedure, a single arteriovenous passageway is formed (i.e., a "first" blood flow passageway) and the lumen of the coronary vein is blocked or closed off immediately proximal to such first blood flow passageway, such that arterial blood will enter the vein and will be forced to flow through the vein, in the retrograde direction. In this manner, the arterial blood from the obstructed artery may retroperfuse the myocardium through the coronary vein. In another variation of the procedure, one or more secondary arteriovenous passageways (e.g., puncture tracts or interstitial tunnels) may be formed between the coronary vein into which the arterial blood has been shunted, and the obstructed artery or another coronary artery. These secondary passageway(s) allow the rerouted arterial blood to re-enter the coronary arterial tree after having bypassed the arterial obstruction. In cases wherein such secondary blood flow passageways are formed, the lumen of the coronary vein may additionally be blocked or closed off at location(s) distal to such secondary passageway(s), to cause the rerouted arterial blood to re-enter the arterial vasculature, as desired.

ii. Procedures Which Require the Formation of an Anastomotic Connection to the Wall of A Luminal Anatomical Structure Various types of anastomotic connections are frequently formed in luminal anatomical structures for the purpose of connecting opposing transected ends or openings formed in anatomical conduit(s) (e.g., blood vessel, intestine, etc.) or for connecting an opening formed in an anatomical conduit to another anatomical structure. When joining the juxtaposed ends or openings of a singular anatomical conduit which has been transected, or when joining the juxtaposed ends or openings of two (2) different anatomical conduits, such joinder(s) may be accomplished by either 1) end-to-end, 2) end-to-side, or 3) side to side anastomosis. Irrespective of which type of anastomotic connection is being formed, the usual surgical technique requires that the luminal anatomical conduit(s) be maneuvered into proximity and placed in abutting juxtaposition, such that the ends or openings of the anatomical conduit(s) are in alignment with one another. Thereafter, sutures, staples or other connecting apparatuses are passed through the walls of the juxtapositioned anatomical conduit(s) to form the desired anastomotic connection therebetween. Anastomotic connections of this type are frequently performed during surgical procedures wherein a diseased or injured segment of an anatomical conduit (e.g., blood vessel, intestine, etc.) has been resected and removed, and the opposing cut ends of the conduit are then reconnected (by end-to-end, side to side, or end to side anastomosis) to permit continued flow of bodily fluids or other matter through the conduit.

iii. Procedures Wherein Grafts or Other Articles are

Attached to A Luminal Anatomical Structure

Examples of medical procedures wherein it is desirable to anchor or attach a graft or other apparatus to the wall of a blood vessel or other luminal anatomical conduit include certain endovascular grafting procedures wherein a tubular graft is placed within the lumen of an aneurysmic blood vessel to create a neo-lumen or artificial flow conduit through the aneurysm, thereby eliminating the exertion of blood pressure on the aneurysm and allowing the aneurysmic space to subsequently become filled in with granulation tissue. These endovascular grafting procedures have heretofore been used to treat aneurysms of the abdominal aorta, as well as aneurysms of the descending thoracic aorta. The endovascular grafts which have heretofore been used for these procedures typically incorporate or are combined with one or more radially expandable stents which are radially expanded in situ to anchor the tubular graft to the wall of the blood vessel at sites upstream and downstream of the aneurysm. However, in the event that these stent(s) fail to establish sound frictional engagement with the blood vessel wall, the graft may undergo undesirable migration or slippage, or blood may leak into the anneurysmic sac (sometimes referred to as an "endoleak").

Thus, in view of the above-mentioned undesirable complications associated with the use of radially expandable stents to frictionally anchor a graft or other apparatus to the wall of a blood vessel (or other luminal anatomical structure) there exists a need in the art for the development of new endoluminal suturing devices which may be used to suture the opposite ends of a endoluminal tube graft (or other article) to the surrounding wall of a blood vessel or other tubular anatomical conduit, thereby ensuring sound and permanent placement of the graft or other article. Also, in view of the other types of medical procedures described hereabove, there also exists a need in the art for the development of new transluminal methods and apparatus for closing the lumen of a luminal structure and/or for forming an anastomotic connections within or to the wall of the luminal structure.

SUMMARY OF THE INVENTION

The present invention provides intraluminal devices and methods which are useable to i) fully or partially close the lumen of a luminal anatomical structure (e.g., a blood vessel), ii) form anastomotic junctions between or connections to luminal anatomical structure(s) and/or iii) attach an endoluminal, extraluminal or transluminal graft or other apparatus to the wall of a luminal anatomical structure.

i.) First Embodiment—Clock Spring Occluder

In accordance with a first embodiment of the invention, there is provided an intraluminal device which is useable to occlude luminal anatomical structure by way of a closure device referred to herein, for purposes of convenience only, as a "clock spring" occluder. This device comprises an elongate catheter which is insertable into a luminal structure, and a resilient coil which is advancable out of the catheter and at least partially through the wall of the luminal anatomical structure to occlude the lumen of the anatomical structure. This resilient coil may optionally have one or more engagement members (e.g., barbs or hooks) formed thereon to enhance its engagement or gripping of the anatomical structure and to prevent the coil from slipping or pulling back through the puncture tract through which it is advanced into or through the anatomical structure wall. Generally, a first end of the resilient coil is advancable out of the catheter and at least partially through the wall of the luminal structure (e.g., blood vessel) within which the catheter is positioned. Thereafter, the coil is further advanced within or outside of the wall of the anatomical structure so as to fully or partially encircle or surround the lumen of the anatomical structure (e.g., it may slidably advance around the adventitial surface of a blood vessel). The optional engagement members (hooks or barbs), if present, will protrude into, grip, adhere to or otherwise engage the wall of the luminal anatomical structure in a manner which will prevent the coil from slipping or pulling back through the puncture tract which it has formed into or through the anatomical structure wall and/or to prevent the from uncoiling in any way which would cause the lumen of the anatomical structure to return to its open configuration.

After the coil has been fully advanced out of the catheter, the catheter may be extracted and removed, leaving the coil in place. The coil is biased to a coiled or closed configuration such that it will then draw the wall of the luminal structure inwardly so as to fully or partially close the lumen of the anatomical structure.

ii. Second Embodiment T-Occluder/Connector Apparatus

In accordance with a second embodiment of the invention, there is provided another intraluminal device, which is useable to occlude or to form anastomoses in/attachments to a luminal anatomical structure. This second embodiment comprises a catheter and an occluder/connector apparatus which is advancable out of the catheter and at least partially through the wall of the luminal anatomical structure to occlude or for attachments to/anastomoses in that anatomical structure. For purposes of convenience only this occluder/connector apparatus will be referred to herebelow as a T-occluder/connector device. In general, this embodiment comprises an elongate catheter having a hollow puncturing member (e.g. a needle) which is advancable out of the catheter and through the wall of the anatomical structure. One or more of the T-occluder/connector device(s) is/are loaded into the lumen of the puncturing member. Each such T-occluder/connector device generally comprises an elongate link (e.g., a thread, wire, strand, cord, etc.) having first and second engagement members (e.g., crossbars, flanges, hooks, barbs, adhesive, clips, etc.) formed on either end thereof. After the catheter has been advanced to the desired site within the luminal structure, the puncturing member is advanced out of the catheter and at least partially through the wall of the luminal structure, at a first location. Thereafter a first one of the engagement members of a T-occluder/connector device is advanced out of the puncturing member to engage the wall of the luminal anatomical structure at a first location. Then, the puncturing member is retracted into the lumen of the anatomical structure and is moved or reoriented therewithin. Thereafter, the puncturing member is advanced (a second time) at least partially through the wall of the luminal anatomical structure, at a second location thereon. Thereafter, the second engagement member of that T-occluder/connector device is expelled from the puncturing member to engage the wall of the anatomical structure at the second location. This procedure may be repeated to install the desired number of T-occluder/connector devices at the desired locations about the wall of the luminal anatomical structure. When the procedure is completed, the puncturing element and catheter are removed, leaving the previously installed T-occluder/connector device(s) in place. Depending on the particular application, the link portion(s) of the T-occluder/connector device(s) may be formed of rigid, pliable, elastic, nonelastic, malleable, nonmalleable, retractable or nonretractable material to exert the desired amount of inward pulling force upon the engagement members. This inward pulling of the engagement members results in the desired occlusion of the lumen of the anatomical structure or the desired anastomosis in or attachment to its wall.

iii.) Third Embodiment—Twist Clip Occluder

In accordance with a third embodiment of the present invention, there is provided another intraluminal device which is useable to occlude the lumen of an anatomical structure (e.g., a blood vessel) by way of a closure device referred to herebelow for purposes of convenience only as a "Twist Clip Occluder". This device generally comprises an elongate catheter having an elongate twistable clip member formed of bendable (i.e., malleable) material loaded in the catheter and advance able from the catheter and at least partially through the wall of the luminal anatomical structure. After the clip member has been advanced into or around the wall of the anatomical structure, the catheter (or a secondary twisting tool) is rotated so as to twist the clip member to a closed configuration wherein it will draw the wall of the luminal anatomical structure inwardly so as to fully or partially close its lumen.

iv. Fourth Embodiment Transluminal Suturing Device

In accordance with a fourth embodiment of the present invention, there are provided catheter-based devices for installing sutures, staples or other connector apparatus into the wall of one or more luminal anatomical structure(s) (e.g., blood vessel(s), intestine(s), duct(s), or other anatomical conduit(s)). For purposes of convenience only, these devices of the present invention will be referred to herein as "intraluminal suturing devices", although it will be appreciated that various types of connector materials (e.g., wire, staples, absorbable sutures, nonabsorbable sutures, etc.) may be installed by use of these devices.

a. Inboard Needle Type

One type of intraluminal suturing device of the present invention comprises an elongate rigid or pliable catheter which is advance able into the lumen of a luminal anatomical structure, and which has i.) a tissue inlet opening into which a portion of the wall of the luminal structure may be caused to intrude (i.e., lapse, invaginate, extend inwardly, etc.) and ii.) an axially reciprocating penetrating member (e.g., a needle) having a suture thread, staple, wire or other connector material attached thereto. The penetrating member is mounted within the catheter, adjacent the tissue inlet opening and generally parallel to the longitudinal axis of the catheter, such that the penetrating member may be alternately passed back and forth through the portion(s) of the luminal structure wall which protrude into the tissue inlet opening. In operation, this inboard needle type device may be used by advancing the catheter into the lumen of the anatomical structure and causing a portion of the wall of the anatomical structure to intrude into the tissue inlet opening of the catheter such that some of the tissue is positioned in the path of the axially reciprocating penetrating member. The penetrating member, with its attached suture thread, staple or other connector material, is then passed through the intruding mass of tissue a first time. If it is desired to pass the suture material or other connector material through the wall of the anatomical structure more than once (e.g., to form an uninterrupted suture line) the catheter may then repositioned within the luminal anatomical structure (e.g., rotated and/or longitudinally advanced and/or longitudinally retracted) and another portion of the wall of the anatomical structure will caused to intrude into the tissue inlet opening such that some of that tissue is located in the path of the axially reciprocating penetrating member. The penetrating member, with its attached suture thread, staple or other connector material, is then once again passed through the intruding mass of tissue. These operational steps are repeated as many times as necessary to form the desired anastomosis or connection.

In some applications, the suture material or other connector material will be drawn taught and knotted in the nature of a "purse string" so as to draw the wall of the anatomical structure inwardly and to fully or partially close its lumen. These operational steps may be repeated numerous times, as necessary, to form the desired anastomosis in, or connection to, the wall(s) of the luminal anatomical structure(s). In other applications, the suture material or other connector material will be knotted or tied (one or more times) without having been drawn taught, so as to allow the lumen to remain open, while forming the desired anastomotic connection in, or attachment to, the wall of the luminal structure.

b. Outboard Needle Type

An alternative type of intraluminal suturing device of the present invention generally comprises an elongate rigid or pliable catheter which is advance able into the lumen of a luminal anatomical structure, such catheter having i.) a first penetrating member lumen from which a penetrating member may pass out of a first opening in the side of the catheter, ii.) a second penetrating member lumen into which the penetrating member may pass through a second opening formed in the side of the catheter, and iii.) a preshaped, pliable penetrating member which is passable a) from the first lumen, b) out of the first opening, c) through an adjacent portion of the wall of the luminal anatomical structure, d) into the second opening and d) into the second lumen. A suture thread, or other connector material as described hereabove, is attached to the penetrating member such that it is drawn by the penetrating member through the tissue.

In operation, this outboard needle type of intraluminal suturing device may be used by advancing the catheter into the lumen of an anatomical structure such that the first and second openings of the catheter are located adjacent a first portion of the wall of the anatomical structure. The penetrating member (and the suture thread or other connector material attached thereto) is then passed from first lumen, out of the first opening, through the first portion of tissue, into the second opening and into the second lumen. In applications where it is desired to pass the suture thread or other connector material repeatedly through the wall of the anatomical structure (e.g., an uninterrupted suture line) the catheter will then be repositioned (e.g., rotated and/or longitudinally advanced and/or longitudinally retracted) such that a second portion of tissue is adjacent the first and second openings of the catheter, and the foregoing procedural steps are then repeated.

v. Fifth Embodiment—Device Useable to Form Attachments or Anastomoses

Further in accordance with the invention, there is provided a device for forming attachments to, or anastomoses in, a luminal anatomical structure. This device generally comprises an elongate catheter wich is insertable into the lumen of the luminal anatomical structure and a hollow needle disposed within said catheter, said needle having a sharpened distal tip, a needle lumen which extends longitudinally therethrough, and an outlet opening formed in communication with said needle lumen. The needle is advancable out of the catheter, after the catheter has been inserted into the luminal anatomical structure, such that the sharpened distal tip of the needle will puncture through the wall of the anatomical structure and the outlet opening of the needle will become situated outside of the luminal anatomical structure. At least one attachment apparatus is initially loaded into the lumen of the needle. Each attachment apparatus generally comprises a flexible link (e.g., a cord, thread, strand, or elongate member) having first and second engagement members (e.g., t-bars, flanges, arms, etc.) formed on opposite ends thereof. These engagement members are able to advance, one at a time, out of the outlet opening of the needle. While loaded in the lumen of the needle, the engagement members may be connected to one another, in a chain-like fashion, so that they may be advanced and/or retracted as a unit. After the catheter has been inserted into the luminal anatomical structure, the needle is advanced (a first time) out of the catheter and through a first location on the wall of the luminal anatomical structure. Thereafter, one engagement member is passed out of the outlet opening of the needle so that it becomes deployed outside of or within the wall of the luminal anatomical structure so as to engage the wall. The needle is then retracted into the catheter and the catheter is repositioned (e.g., rotated and/or longitudinally advanced/retracted) within the lumen of the anatomical structure. The needle is then advanced (a second time) out of the catheter and through a second location on the wall of the luminal anatomical structure. The second engagement member is then advanced out of the outlet opening of the needle so that it becomes deployed outside or within the wall of the anatomical structure and will engage the wall, adjacent the second location. The needle is then retracted into the catheter, leaving the two (2) engagement members in abutting engagement with the first and second loactions on the wall of the atomical structure, with the link portion of the attachment member traversing therebetween. Depending on the number of attachment members required to form the desired attachment or anastomosis, this procedure may then be repeated one or more times. When the desired attachment or anastomosis has been completed, the catheter and accompanying needle are removed from the body, leaving the previously installed attachment members in place. The attachment members may be formed of absorbable or non-absorbable material, depending of the nature of the application.

This embodiment of the invention may be used to attach various items (e.g., endoluminal grafts, stents) to the wall of a luminal anatomical structure, or may be utilized to form an anastomotic junction between the approximated ends of one or more anatomical conduit(s) (e.g., the opposing cut ends of a blood vessel, fallopian tube, ureter, urethra, pancreatic duct, common bile duct, esophagus, intestine, or other conduit which has been cut or resected). Further objects and advantages of the present invention may become apparent to those skilled in the art upon reading and understanding of the following detailed description, and the accompanying drawings.

BRIEF DESCRIPTION OF THE DRAWINGS

FIG. 1 is a partial longitudinal sectional view of an adjacent artery and vein wherein a lumen closing device has been used to install a clock-spring occluder apparatus of the present invention to close the lumen of the vein.

FIGS. 2–5 are a step-by-step showing of a preferred method for using the device of FIG. 1 to accomplish closure of a blood vessel.

FIG. 7 is a partial perspective view of intraluminal device of the present invention which incorporates a T-occluder apparatus for closing the lumen of a blood vessel.

FIGS. 8–11 are step-by-step showings of a method by which the device of FIG. 7 is used to effect closure of the lumen of a blood vessel using a T-occluder apparatus having an elastic link.

FIG. 21 is an enlarged longitudinal sectional view of the distal portion of the device shown in FIGS. 18–18a, operatively positioned within a blood vessel.

FIGS. 23a–23h are partial longitudinal sectional views showing, in step-by-step fashion, a preferred method of using an intraluminal suturing device of the present invention having an outboard tissue penetrating member.

FIG. 24a is a cross-sectional view through line 24a—24a of FIG. 23a.

FIG. 24b is a cross-sectional view through line 24b—24b of FIG. 23a.

FIG. 27b is an end perspective view of the showing of FIG. 27a.

DETAILED DESCRIPTION OF THE PREFERRED EMBODIMENTS

The detailed description set forth below in connection with the appended drawings is intended merely as a description of the presently preferred embodiments of the invention, and is not intended to represent the only forms in which the present invention may be constructed or utilized. This description makes reference to the structural and functional elements of a number of presently preferred or exemplary embodiments of the invention. It is to be understood, however, that the same or equivalent structure and/or function may be accomplished by numerous other embodiments of the invention which are not specifically described herebelow, but which are intended to be encompassed within the spirit and scope of the invention.

i. First Embodiment—Clock Spring Occluder

Figure 2:
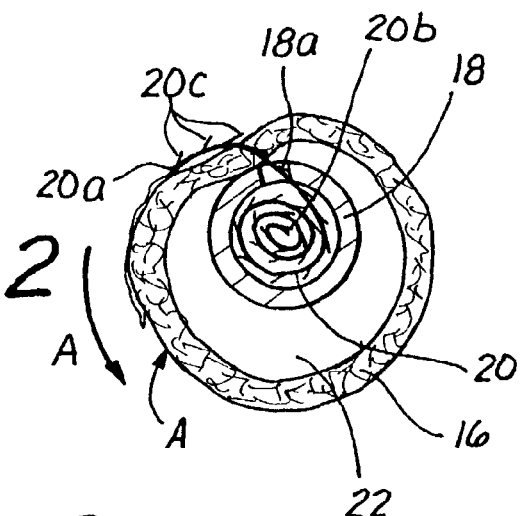
Figure 3:
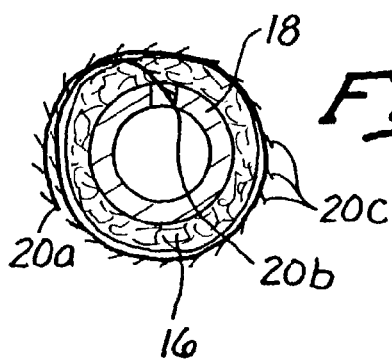

A clock spring occluder 20, more clearly seen in FIG. 2a, comprises a generally spiral-shaped coil having a first outwardly oriented end 20a and a second inwardly oriented end 20b. The clock spring occluder may further have a multiplicity of outwardly extending engagement members, such as protrusions or barbs 20c which, as will be discussed below, enhance the ability of the occluder 20 to securely grasp and occlude the lumen of an anatomical structure such as a blood vessel.

Figure 1A:
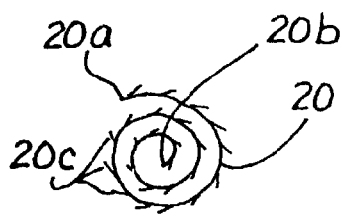
FIG. 1a is an elevational view of a preferred clock spring occluder apparatus of the present invention, which forms a component of the device shown in FIG. 1.

The clock spring occluder 20 is deployed through the lumen of the catheter 18, as shown schematically in FIG. 1. The catheter 18 is inserted and positioned within the vessel 16 such that side opening 18a formed at the distal end of the catheter 18 is aligned with and juxtapositioned with a portion of the vessel wall 16, at the location where it is desired to occlude the vessel. The first outwardly oriented end 20a of the clock spring occluder 20 is then advanced through the side opening 18a of the catheter 18 and through at least a portion of the vessel wall 16. To facilitate such puncture through vessel wall 16, the outward end 20a of the device 20 may optionally be sharpened. The clock spring occluder 20 is then advanced through the puncture site so that it fully or partially surrounds the lumen 22 of the vessel and engages the vessel wall.

Figure 4:
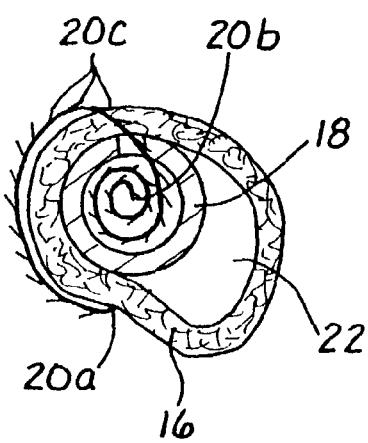

The occluder device 20 is biased to a coiled configuration which causes it to pull the wall of the vessel inwardly so as to collapse and close the lumen of the vessel at the desired location, as shown in FIG. 4.

Figure 6:
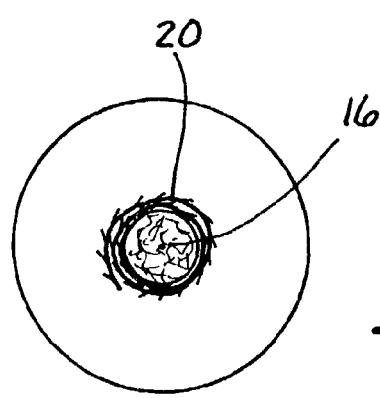
FIG. 6 is a cross sectional view through line 6—6 of FIG. 5.
Figure 11:
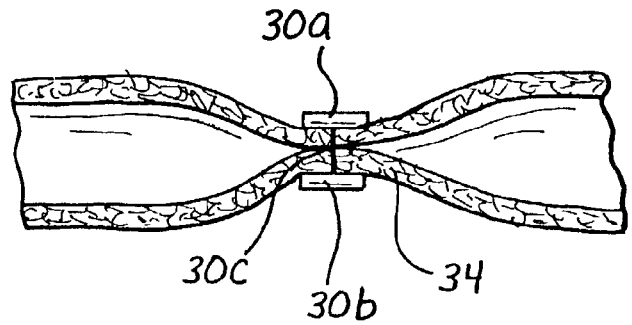
Figure 12:
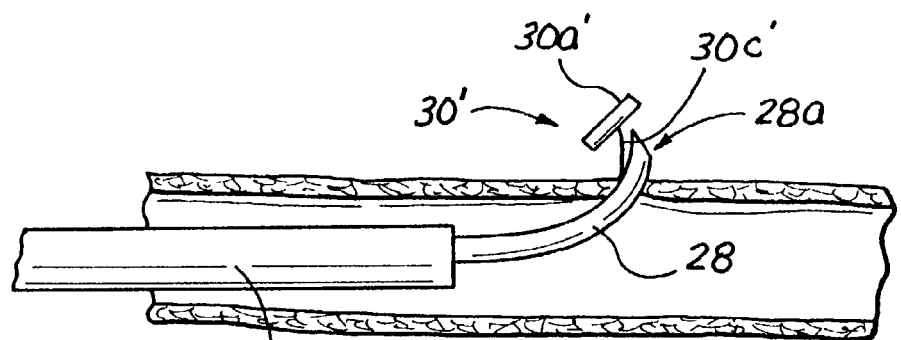
FIGS. 12–17 are step-by-step showings of a method for using the device of FIG. 7 to effect closure of the lumen of a blood vessel using a T-occluder apparatus having a twistable or knottable link.
Figure 13:
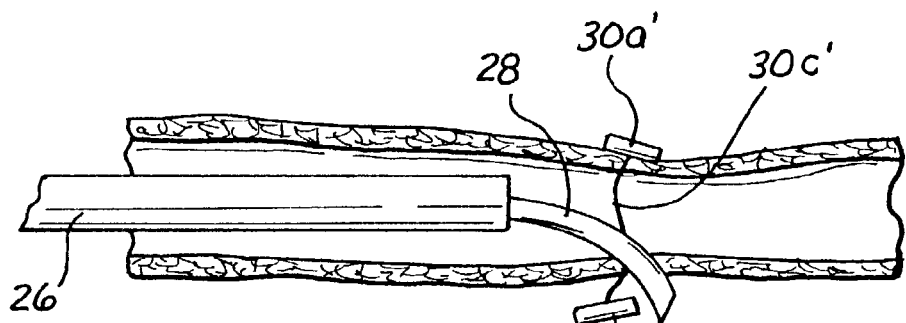
Figure 14:
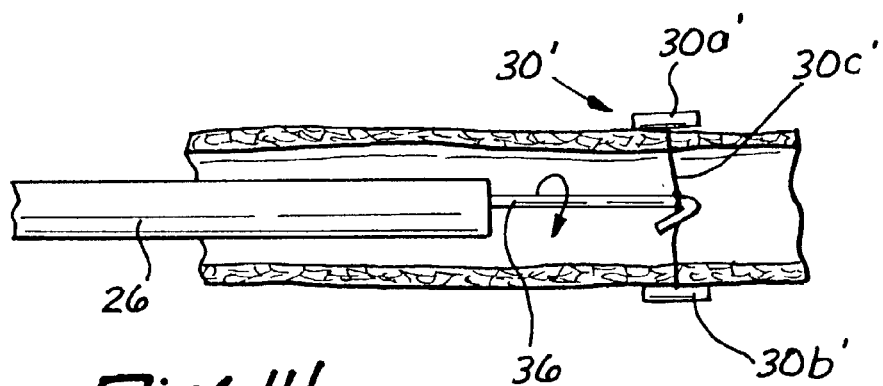
Figure 15:
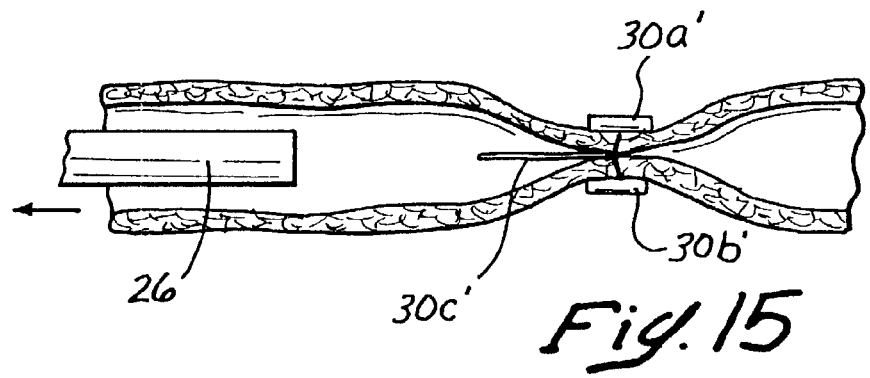

To enhance the ability of the clock spring occluder 20 to engage and pull the vessel wall, one or more engagement members, such as outwardly projecting barbs 20c may be formed on the occluder device 20 to prevent the device 20 from migrating, slipping or pulling through the wall 16 of the vessel. Once the entire length of the clock spring occluder 20 has been advanced through the side opening 18a, the catheter 18 is then removed, as illustrated in FIG. 5. After the catheter 18 has been removed, the occluder 20 will resiliently retract to its preformed coiled configuration to cause the vessel to assume a closed "hourglass" shape, as further illustrated by FIG. 6. The tightness of the coiled configuration of the occluder device 20 will determine whether the lumen of the vessel is fully or partially occluded, as desired.

ii. Second Embodiment—T-Occluder Apparatus

FIGS. 7–11 and 23–23b show a second embodiment of a transluminal device 24 which is useable for ligating a luminal structure, such as a blood vessel, or for the other applications such as anchoring or attaching an endoluminal graft or other endoluminal apparatus to the wall of the luminal structure (e.g., blood vessel).

This second embodiment of the intraluminal device 24 comprises an elongate rigid or pliable catheter 26 having a first lumen 26a and a second lumen 26b extending longitudinally therethrough. A hollow needle 28, which has an elongate slot 28b formed in one side thereof adjacent its distal end 28a, is slidably disposed within the first lumen 26a of the catheter 26 so as to be advancable out of the catheter, as shown. The second lumen 26b may be used for passage of a guidewire, to permit the catheter 26 to be advanced over a pre-positioned guidewire.

Disposed within the hollow bore of the curved needle 28 is a T-occluder apparatus 30 or 30'. The T-occluder apparatus generally comprises an elongate link member such as a pliable cord 30c and first 30a, 30a' and second 30b, 30b' engagement members attached to the other end thereof. In the particular design shown in the drawings, the engagement members 30a, 30a', 30b, 30b' are in the form of cross members, but it will be appreciated that these engagement members 30a, 30a', 30b, 30b' may be any suitable type of structure or material (e.g., projection, flange, hook, barb, adhesive, staple, etc.) capable of engaging and/or connecting ti the wall of the luminal anatomical structure to be occluded. In the particular embodiment shown, the cross-members 30a, 30a', 30b, 30b' are initially disposed in direct alignment within the hollow inner bore of the needle 28, such that the cross-members 30a, 30a', 30b, 30b' are in serial end-to-end alignment within the bore, and are substantially parallel to the longitudinal axis of the needle 28. In this manner, some or all of the cord 30c may protrude out of the elongate slot 28b formed in the side of the needle, in the manner shown in FIG. 7.

A push rod 32 is slidably disposed within the bore of the needle 28, behind the T-occluder apparatus 30, 30' loaded therewithin. In this manner, the push rod 28 may be utilized to expel the first and second cross-members 30a,30a',30b, 30b' out of the distal end 28a of the needle 28.

In one design shown in FIGS. 7–11, the cord 30c may be formed of elastic material which is elastically biased to a shortened configuration such that the cord 30c will pull or draw the cross-members 30a, 30b inwardly toward a common central point or location. In another design shown in FIGS. 12–15 the cord 30c' may be formed of material which is capable of being wound (i.e., a malleable material which can be plastically deformed, twined or kinked—or a pliable material capable of being tied or knotted) such that the overall length of the cord 30c' becomes shortened, thereby drawing the cross members 30a', 30b' inwardly toward a common central point or location.

In normal operation, the catheter 26 is advanced to its desired location within a blood vessel or other luminal anatomical structure. The positioning of the catheter 26 may be guided or verified by any suitable imaging or guidance system and, optionally, a fiberoptic endoscope, ultrasound imaging system, or any other on-board imaging system may be incorporated into the catheter to provide an image of the area adjacent a view port 26b or other imaging location on the catheter 26. (see FIG. 7) Once the catheter 26 has been placed in the desired position, the needle 28 is advanced out of the catheter 26 and the distal end 28a of the needle is passed fully or partially through the wall of the luminal anatomical structure, at a first location. The push rod 32 is then advanced through needle 28 in the distal direction such that the first engagement member 30a, 30a' of the first T-occluder 30, 30' is expelled out of the needle 28 so that it will engage the wall of the luminal anatomical structure, adjacent the first location. Therereafter, as shown in FIG. 9, the needle 28 is retracted into the lumen of the anatomical structure 34 and the catheter is moved (e.g., rotated approximately 180 degrees). Thereafter, the needle 28 is once again advanced such that the distal end 28a of the needle 28 passes fully or partially through the wall of the luminal anatomical structure 34 at a second location which is diametrically opposite the first location. (see FIGS. 10 and 13) The push rod 32 is then once again advanced in the distal direction to expel the second engagement member 30b, 30b' out of the distal end 28a of the needle and into engagement with the wall of the anatomical structure 34 adjacent the second location.

When the design of FIGS. 7–11 is installed in the foregoing manner, the elastic cord 30c will resiliently shorten and will pull the engagement members 30a, 30b inwardly so as to collapse the wall of the anatomical structure 34 and fully or partially close its lumen, as desired.

When the design of FIGS. 12–15 is installed in the foregoing manner, the needle 28 will then be withdrawn from or retracted into the catheter 26 and a winding tool 36 will then be advanced from the catheter into contact with the windable cord 30c'. This winding tool 36 may be a hook (as shown) or any other suitable apparatus capable of twining, deforming, crimping, tying or knotting the cord 30c'—in accordance with the particular type of material of which the cord 30c' is formed (e.g., plastically deformable or pliable/knottable). This winding tool 36 is then used to wind (i.e., plastically deform, knot, twine or tie) the cord 30c' in a manner which causes the cord 30c' to shorten, thereby pulling the engagement members 30a', 30b' inwardly to cause the wall of the anatomical structure 34 to collapse and its lumen to become fully or partially closed, as desired. As will be recognized, the winding tool 36 may then be disengaged from the wound cord 30c' and removed, or alternatively may be designed to be detached from the catheter 26 and left in place within the wound cord 30c'. In this regard, the winding tool 36 may be configured to detach from the catheter 36 by separation of a weakened "tear away" area formed in the tool 36 such that the distal portion of the tool 36 will break away when sufficient proximally directed or rotational force is applied thereto. In this respect, it will be recognized that the force necessary to break winding tool 36 will be less than the force necessary to dislodge the hook member 36 from the attachment cord 30c' that is wrapped thereabout.

iii. Third Embodiment—Twist Clip Apparatus

Figure 16:
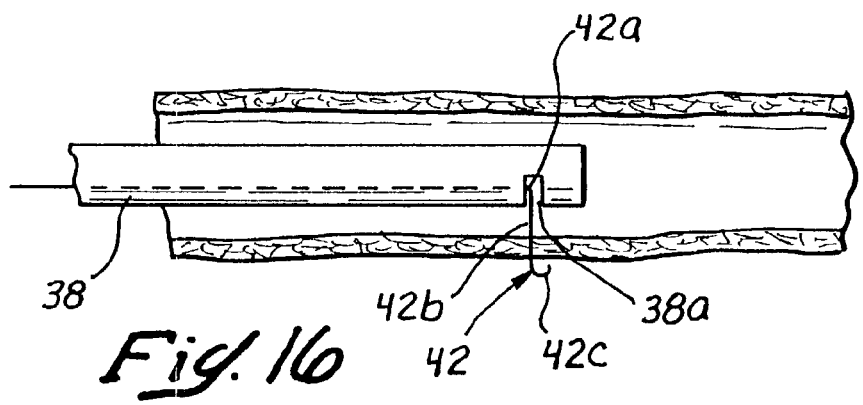
Figure 17:
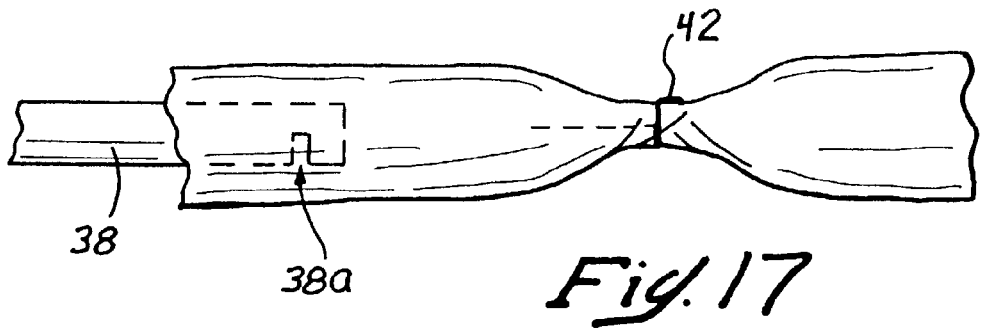

Referring now to FIGS. 16 and 17, there is shown a third embodiment on an intraluminal apparatus for occluding blood flow at a specific site within a luminal anatomical structure such as a blood vessel. As shown in FIG. 16, third embodiment may comprise an elongate rigid or pliable catheter 38 having a hollow lumen extending longitudinally therethrough and a side opening 38a formed near its distal end. Disposed within the lumen of the catheter 38 is a twist clip 42. The twist clip 42 is formed of malleable material and comprises a first straight section 42a and a second section 28b, which extends generally perpendicular to the first straight section 42a. An outwardly curved tip 42c is formed on the distal end of the second section 42b. As illustrated, the twist clip 42, and more particularly the outwardly curved tip 42c thereof, is initially advanced some distance out of the side opening 38a and to pierce through the vessel wall 40. Thereafter, the catheter 38 is rotated, as indicated by the arrow on FIG. 14, so that the clip 42 advances fully or partially around the wall of the anatomical structure 40 to cause its lumen to become fully or partially closed, as shown in FIG. 17. By virtue of the shape of the outwardly curved tip 42c, the clip 42 is thus secured to the outside of the wall while simultaneously forming an intraluminal closure. After such intraluminal closure is formed, the catheter 38 is axially retracted through the lumen of the anatomical structure 40, causing the twist clip 42 to detach and remain embedded within or about the wall of the anatomical structure 40, as shown. As will be recognized, twist clip 42 may be configured to detach from catheter 38 by forming a weakened or break-away area in the clip such that the clip 42 will break away when sufficient proximally directed or rotational force is applied thereto. In this respect, it will be recognized that the force necessary to break twist clip 42 free from the catheter 38 will be less than the tension necessary to dislodge the clip 42 from the wall of the anatomical structure 40.

iii. Fourth Embodiment—Intraluminal Suturing Device

FIGS. 18–22b are directed to an intraluminal suturing device 50, 50' having an inboard penetrating member 54, 54', and FIGS. 23a–26 are directed to an alternative intraluminal suturing device 50" having an outboard penetrating member 530. These intraluminal suturing devices may be used to repair tears or ruptures in anatomical conduits, to occlude anatomical conduits (see, FIGS. 19a–19b described herebelow), to anastomose or join approximated segments of anatomical conduit (see, FIG. 18a (line AN) and/or FIGS. 28a–29b described herebelow) or to anchor or attach various articles (e.g., an endovascular graft) to the wall of an anatomical conduit (see, FIGS. 20, 27a and 27b described herebelow).

a. Inboard Needle Type:

As shown in FIGS. 18–21d and 22–22c, these devices 50, 50' generally comprise an elongate pliable catheter body 52, 52' having a proximal end PE, a distal end DE, and a hollow lumen 54, 54' which extends longitudinally therethrough. A side opening 56, 56' is formed on one side of the catheter body 52, 52' near the distal end DE thereof. A balloon 58, 58' or other suitable type of lateral pressure exerting member (e.g., an extendable foot) may optionally be mounted on the outer surface of the catheter body 52, 52' at a location which is substantially diametrically opposite the location of the side opening 56, 56'. An axially moveable needle advancement/retraction member 64 or 64' is mounted within the lumen 54, 54' of the catheter body 52, 52'. A tissue penetrating member such as a needle, 74, 74' is mounted within the lumen 54, 54' of the catheter body 52, 52' and is axially moveable back and forth, by way of the needle advancement/retraction member 64, 64'. The needle 74, 74' is reciprocally moveable back and forth between i) a first position wherein the needle 74, 74' is proximal to the side opening 56, 56', and ii) a second position wherein the needle 74, 74' is distal to the side opening 56, 56'.

A first portion of the wall of the luminal anatomical structure (e.g., blood vessel) wherein the catheter body 52, 52' is positioned may be drawn or otherwise caused to intrude (e.g., invaginate, lapse) into the side opening 56, 56' such that the needle 74, 74' may be advanced or retracted through the intruding portion of tissue. In this manner, a length of connector material 88, 88' such as suture thread, which is attached to the needle 74, 74', will be drawn through the intruding tissue to form a stitch in the wall of the luminal anatomical structure. In embodiments wherein the suture line is to be used to close or occlude the anatomical structure, the a continuous suture 88, 88" will be passed through multiple locations about the wall of the anatomical structure and the suture 88, 88' will be drawn taught in the nature of a "purse string", thereby collapsing the wall of the anatomical structure inwardly and causing its lumen to become fully or partially closed, as desired. In other applications, wherein the suture material 88, 88' is to be used to attach or anchor an article or apparatus (e.g., an endoluminal tube graft) to the wall of the luminal anatomical structure, such article or apparatus will be pre-positioned adjacent the wall of the anatomical structure and the intraluminal suturing device will be used to place continuous or interrupted stitches through the article/apparatus and the wall of the anatomical structure, so as to anchor the article/apparatus to the anatomical structure as desired.

Figure 18:
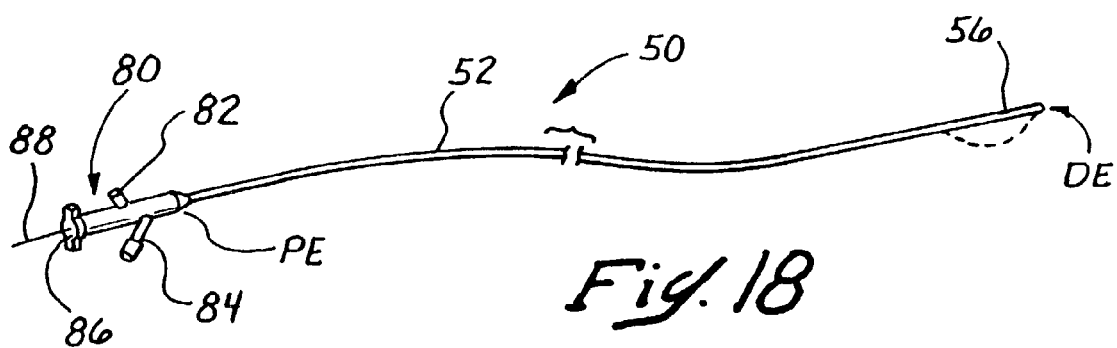
FIG. 18 is a perspective view of an intraluminal suturing device of the present invention having an inboard tissue-penetrating element which is useable to pass a connector material (e.g., suture thread) through the wall of a luminal anatomical structure.
Figure 18A:
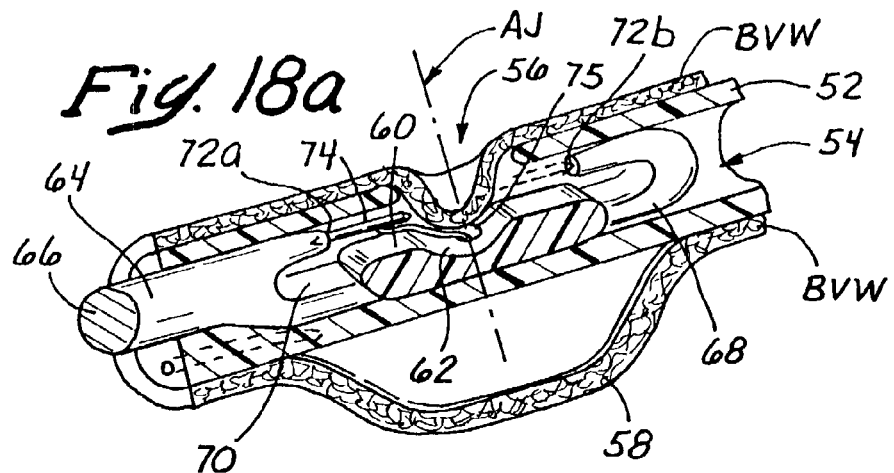
FIG. 18a is a longitudinal sectional view of a portion of the device of FIG. 18.

In the particular embodiment shown in FIGS. 18–18a the needle advancing/retracting member 64 comprises an elongate shaft 66 having a bifurcated, generally "C" shaped distal portion 68. This C-shaped distal portion 68 comprises a generally "C" shaped member 70 having first and second needle abutting indentations 72a, 72b formed on its directly opposing ends, as shown. A cross-member 60 is formed within or attached to the tubular catheter body 52 on opposite side thereof, such that the cross-member 60 traverses the lumen 54 of the catheter at a location directly beneath the side opening 56. An indentation 62 is formed in the upper surface of the cross-member 60 immediately beneath the side opening 56. The "C" shaped distal portion 68 of the needle advancing/retracting member 64 partially surrounds the cross-member 60, as shown. A dual-tipped needle 74 is mounted within the lumen 54 above the cross-member 60. Needle abutting surfaces 72a, 72b of the C-shaped portion 68 of the needle advancing/retracting member 64 are preferably of a concave shape so as to axially receive the sharpened ends of the needle 74. In this manner, when the needle advancing/retracting member 64 is advanced in the distal direction, the first needle abutting surface 72a will push the needle 74 past the side opening 56 and to an advanced position distal to the side opening 56, but still within the lumen 54 of the catheter body 52. Thereafter, when the needle advancing/retracting member 64 is retracted in the proximal direction, the second needle abutting surface 72b will drive the needle 74 in the proximal direction, past the side opening 56, and to a retracted position which is proximal to the side opening 56, but still within the lumen 54 of the catheter body 52.

A proximal connector assembly 80 may be mounted on the proximal end PE of the catheter body 52. Such proximal connector assembly 80 incorporates a slidable actuator knob 82 which is connected to the needle advancing/retracting member 64 such that when the actuation knob 82 is advanced in the distal direction, the needle advancing/retracting member 64 will advance in the distal direction, and when the actuation knob 82 is retracted in the proximal direction, the needle advancing/retracting member 64 will retract in the proximal direction. Additionally, the preferred proximal connector assembly 80 may have a balloon inflation port 84 connected to a balloon inflation lumen 89 which extends longitudinally through the catheter body 52 and which terminates distally in the interior of the balloon 58. In this manner, balloon inflation fluid may be injected and withdrawn through the balloon inflation port 84 to effect inflation and deflation of the balloon 58, as desired. A suture passage aperture 75 is formed vertically through the cross-member 60 at a location immediately beneath the center of the side opening 56 and the strand of suture material 88 which extends into the proximal port of the proximal connector assembly 80 continues through the suture lumen 53 of the catheter body, upwardly through the suture passage aperture 75 formed in cross-member 60, and is attached to the dual tip needle 74 at a location between the opposite sharpened ends of the needle 74, and preferably at the approximate longitudinal mid-point of the needle 74.

The device of FIGS. 18–18a may be utilized to place suture(s) in the wall of a blood vessel by inserting the pliable catheter body 52 into the patient's vasculature and advancing the catheter body 52 through the vasculature until the side opening 56 is located at the site at which the first stitch is to be placed. In some instances, the diameter of the catheter body 52 will be as large as the inner diameter of the blood vessel lumen such that a portion of the blood vessel wall will automatically intrude into the side opening of the catheter body. In other instances, the diameter of the catheter body 52 will be less than the inner diameter of the blood vessel and the side balloon 58 will be used to compress the catheter laterally against the wall of the vessel. In this regard, a syringe may be attached to the balloon inflation port 84 and utilized to infuse a balloon inflation fluid (e.g., saline solution) into the balloon 58 to inflate the balloon 58.

The inflated balloon 58 will contact the wall of the vessel and will propel the catheter body 52 laterally against the wall of the vessel opposite the location of the balloon 58. In this manner, the side opening 56 will become compressed against the blood vessel wall BVW and a portion of the tissue of the blood vessel wall BVW will intrude (e.g., invaginate or lapse) into the side opening 56 and into the lumen 54 of the catheter int he path of the needle 74. To facilitate such intrusion of the blood vessel wall BVW into the side opening 56 suction may optionally be applied to the lumen 54 of the catheter body.

Figure 19A:
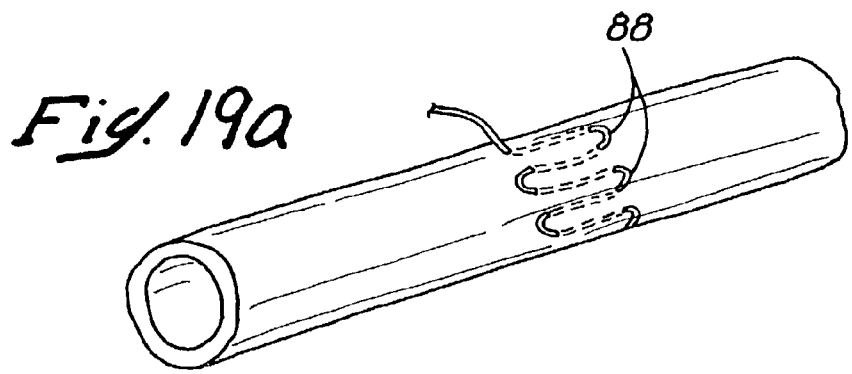
FIG. 19a-19b are step-by-step showings of a preferred method of using the device of FIGS. 18–18a to place a continuous "purse string" suture which is useable to ligate the lumen of the anatomical structure.
Figure 19B:
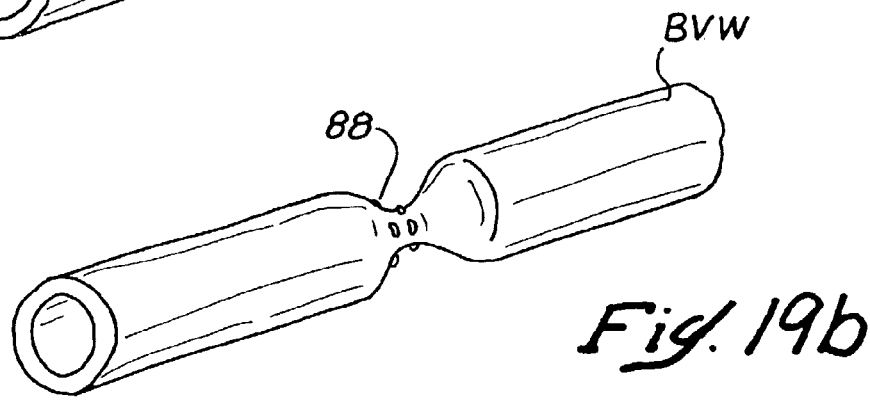
Figure 20:
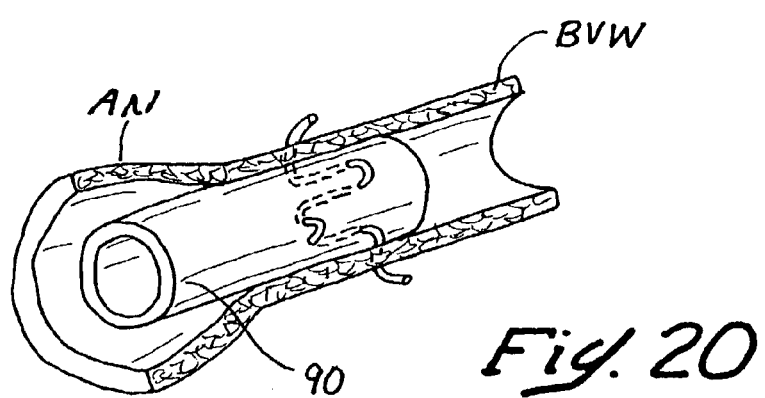
FIG. 20 is a longitudinal sectional view of a segment of a blood vessel illustrating the manner in which the device of FIGS. 18–18a may be used to suture the ends of an endoluminal tube graft within a blood vessel so as to bridge an aneurysm.
Figure 21A:
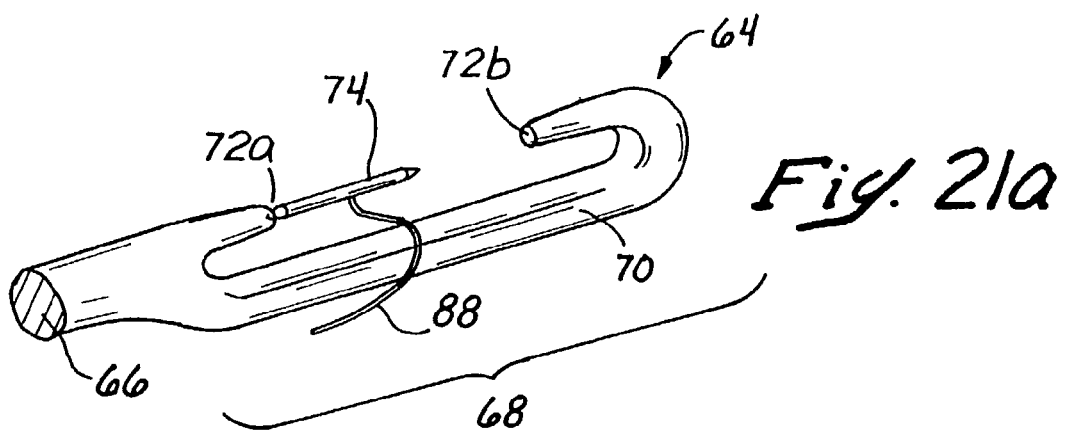
FIG. 21a is a perspective view of the C-shaped distal segment of the preferred needle advancing/retracing component of the device of FIGS. 18–18a & 21.
Figure 21B:
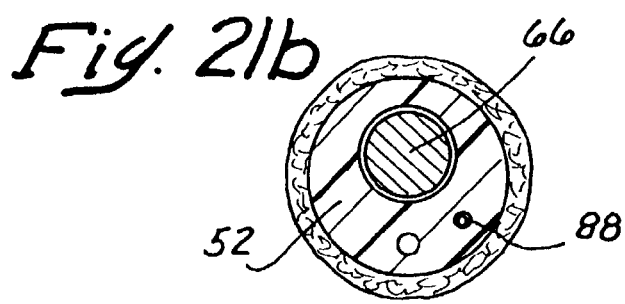
FIG. 21b is a cross sectional view through line 21b—21b of FIG. 21.
Figure 21C:
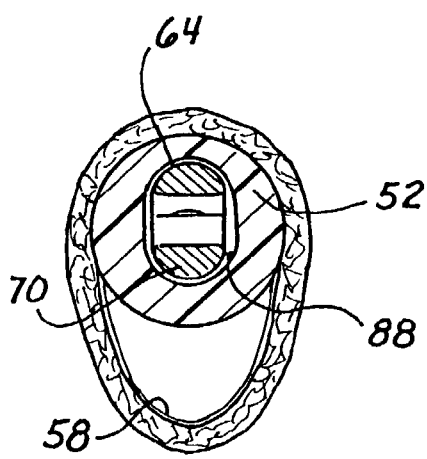
FIG. 21c is a cross sectional view through line 21c—21c of FIG. 21.
Figure 21D:
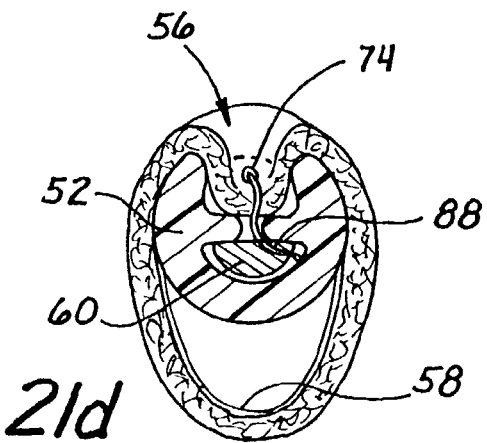
FIG. 21d is a cross sectional view through line 21d—21d of FIG. 21.

After the blood vessel wall BVW has been caused to intrude inwardly into the side opening 56, the operator will advance the actuator knob 52 in the distal direction so as to cause the needle advancing/retracting member 64 to also advance in the distal direction. In this manner, the first needle abutting surface 72a of the needle advancing/retracting member 64 will abut against the first sharpened end of the needle 74 and will drive the needle in the distal direction, through the portion of the blood vessel wall BVW which intrudes into the lumen 54 of the catheter body 52. After the needle 74 has been fully advanced through the intruding tissue of the blood vessel wall BVW, the balloon 58 may be deflated (if used) and any optional suction will be terminated. Thereafter, the catheter body will be repositioned (e.g., rotated slightly and/or moved longitudinally) so that the side opening 56 becomes positioned next to a second location on the blood vessel wall BVW. The balloon 58 may be once again inflated (if necessary) so as to press the side opening 56 of the catheter body 52 laterally against the second location on the blood vessel wall BVW, and any optional suction may be applied so as to cause another portion of the blood vessel wall BVW to intrude inwardly into the side opening 56. Thereafter, the operator will retract the actuator knob 82 so as to cause the needle advancing/retracting member 64 to retract in the proximal direction driving the needle 74 in the proximal direction, through the second portion of the blood vessel wall BVW which has been caused to intrude inwardly through the side opening 56. After the needle 74 has been fully advanced through such intruding tissue, the balloon 58 will be once again deflated (if used) and any optional suction will be terminated. Thereafter, the catheter body 52 may again be repositioned, and the above-described procedure repeated as many times as necessary to form the desired suture line in the blood vessel wall BVW. After the desired stitch or suture line has been installed, the device 50 may be retracted and a knot pusher of the type commonly used in laparoscopic surgery may be utilized to form a tie or knot in the suture material 88. In applications wherein it is desired to use the suture material 88 to draw the lumen of the blood vessel closed, the suture 88 may be pulled taught in a purse string fashion, so as to collapse and close the lumen of the blood vessel in the manner shown in FIG. 19b. In other applications, the suture material may interrupted or continuous and may be tied off or knotted using the knot pusher, without drawing the lumen of the blood vessel closed. This procedure may be used to form a radial purse string closure or anastomosis in a blood vessel as shown in FIGS. 19–1 9a. Alternatively, this procedure may be used to anchor an article or apparatus, such as an endoluminal graft 90 for bridging of an aneurism AN, as shown in FIG. 20. The procedure illustrated in FIG. 20 may offer advantages over prior art methods wherein endoluminal grafts were held in place or anchored by way of a radially expandable stent for frictional engagement of the graft 90 to the blood vessel wall BVW. In this regard, the intraluminal suturing devices 50, 50', 50" may be used to sew the opposite ends of a pliable tube graft (e.g., woven polyester or expanded polytetrafluoroethylene (ePTFE)) to the blood vessel wall BVW so as to anchor and hold the tube graft 90 at its desired position, without the need for radially expandable stents or other hardware required for frictionally engaging or anchoring the graft 80 to the blood vessel wall BVW.

Figure 22A:
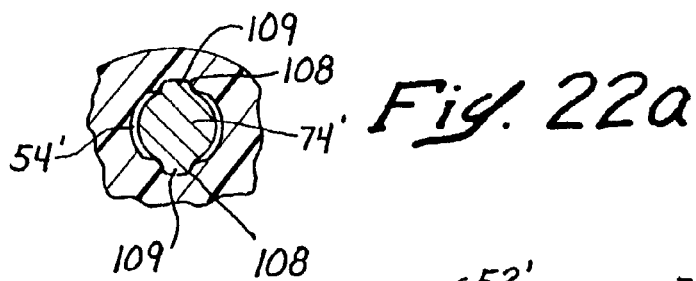
FIG. 22 is a perspective view of another intraluminal suturing device of the present invention, having an inboard tissue penetrating member which is moved by way of a modified advancing/retracting component.
Figure 22B:
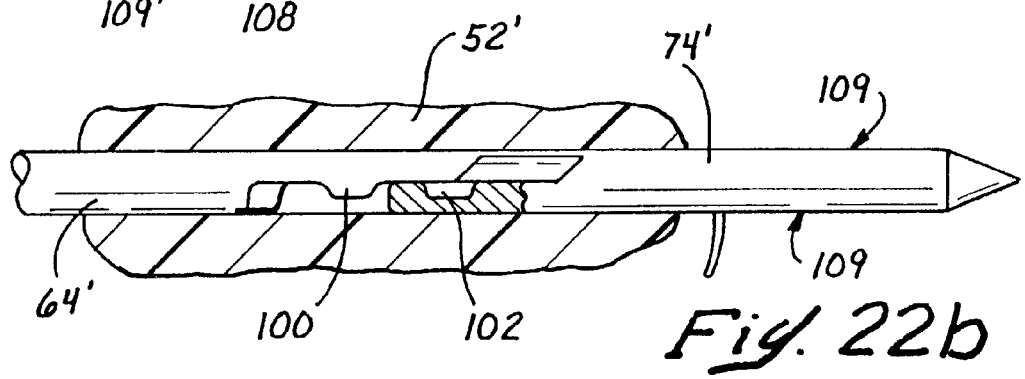
Figure 22C:
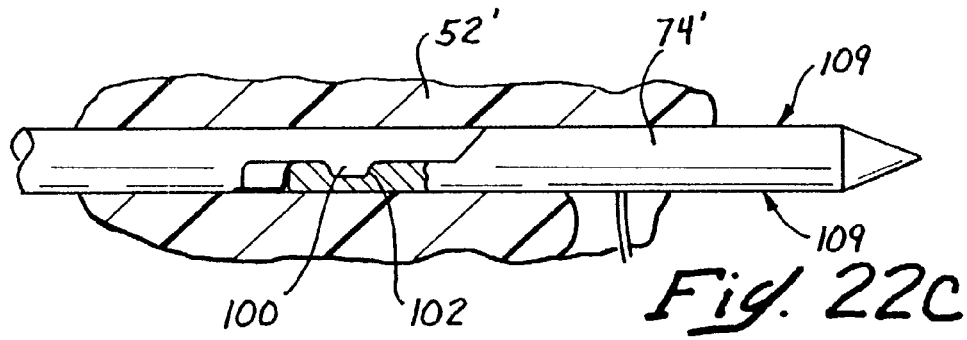

FIGS. 22, 22a, and 22b show a variation of the above-described forth embodiment wherein the intraluminal suturing device 50' has a modified catheter body 52' which has a proximal end PE, a distal end DE, a main lumen 54' extending longitudinally therethrough. A side opening 56' is formed into the main lumen 54' at a first location on one side of the catheter body 52', and an optional balloon 58' may be formed on the catheter body 52' at a location diametrically opposite the side opening 56'. As in the above-described fourth embodiment, a balloon inflation lumen 89' extends longitudinally through the catheter body 52' to permit inflation fluid to be infused into and withdrawn from the balloon 58'. In this variation, the needle advancing/retracting member 64' has a sharpened distal tip 67. A first needle connector is formed on the needle advancing/retracting member 64' near its distal end 67 and a corresponding second needle connector (e.g., a notch) 102 is formed adjacent the proximal end of the needle 74'. Additionally, needle holding members 108 are formed within the main lumen 54' of the catheter body 52' at a position distal to the side opening 56', such needle holding members 108 being constructed to frictionally engage and prevent rotation of the needle 74' while in its second position distal to the side opening 56'. The suture material 88' is attached to the needle 74' at a location between its proximal end 107 and distal end 106, and preferably at the approximate mid-point of the needle 74'.

When this variation of the fourth embodiment shown in FIGS. 22, 22a, 22b is used to place sutures in a blood vessel, the catheter body 52' will be advanced transluminally through the vasculature until the side opening 56 is positioned at the site at which it is desired to place sutures through the wall of the blood vessel. Thereafter, the balloon inflation fluid may be infused (if needed) through the balloon inflation lumen 89' to inflate the balloon 58', thereby compressing the side opening 56' against a first location on the blood vessel wall in a manner which causes the blood vessel wall to intrude into the main lumen 54'. Optionally, suction may be applied to the main lumen 54' to draw the tissue inwardly through the side opening 56'. Thereafter, the needle advancing/retracting member 64' is advanced in the distal direction so as to drive the needle 74' through the portion of the blood vessel wall which has been drawn through the side opening 56' and to its second position located distal to the side opening 56'. After the needle has been advanced to such second position, the needle holding members 108 will frictionally engage and prevent rotation of the needle, and the needle advancing/retracting member 64' will be slightly rotated so as to disengage the first and second needle connectors 100, 102 from each other, thereby releasing the needle advancement/retraction member 64' from the needle 74'. Thereafter, the needle advancing/retracting member is withdrawn proximally to a position proximal to the side opening 56'. Thereafter, the balloon 58' is deflated (if previously inflated), and the catheter body 52' is repositioned such that the side opening 56' is positioned adjacent a second location on the blood vessel wall. Thereafter the balloon 58' is once again inflated (if necessary) and any optional suction desired may be applied to the main lumen 54' so as to draw a second portion of the blood vessel wall into the main lumen 54' through the side opening 56'.

Thereafter, the needle advancing/retracting member 64' is advanced in the distal direction such that the sharpened distal tip 67 of the needle advancing/retracting member 64' will pass through the intruding tissue. After the needle advancing/retracting member 64' has been advanced until its needle connector 100 is located in alignment with the needle connector 102 formed on the proximal end of the needle 74', the needle advancing/retracting member 64' will be slightly rotated so as to engage its needle connecting member 100 with that 102 of the needle 74', thus reconnecting the advancing/retracting member 64' to the needle 74'. Thereafter, the needle advancing/retracting member 64' is again withdrawn in a proximal direction so as to pull the needle 74' back through the tissue and to its first position wherein the needle 74' is positioned proximal to the side opening 56'. Thereafter, the above-described steps are again repeated as many times as necessary to form the desired stitch or suture line in the blood vessel wall.

After the desired stitch or suture line has been placed in the wall of the blood vessel, the catheter 52' may be removed and the suture may be drawn closed so as to ligate the blood vessel, or otherwise tied or knotted to anchor or affix an article or apparatus to the wall of the blood vessel, as described in detail hereabove.

b. Outboard Needle Type:

FIGS. 23a–26 show another intraluminal suturing device 50''' of the present invention, which incorporates an "outboard" tissue penetrating member or needle 530 that extends out of the catheter body 502 so as to pass connector material such as suture thread 529 through the wall of a luminal anatomical structure, such as a blood vessel, within which the catheter body 502 is inserted. In this manner, this device 50''' does not require that any portion of the wall of the luminal anatomical structure be caused to intrude into the catheter body, as with the above-described inboard needle embodiments of the device 50, 50''.

As shown, this device 50''' comprises an elongate, rigid or pliable, catheter body 502 having an irregularly shaped main lumen 504 formed within a distal portion of the catheter body 102. In the embodiment shown, the main lumen 502 is generally of an hourglass or dumbbell cross-sectional shape which defines an upper portion 506, a lower portion 508 and a communicating channel 510 which extends between the upper portion 506 and the lower portion 508. This main lumen 504 is formed in its entirety only in a distal portion of the catheter body 502 and all portions of the main lumen 504 terminate distally in a closed distal end 505. The upper portion 506 and the communicating channel 510 terminate proximally in a closed proximal end 507 within the catheter body 502, but the lower portion 508 continues through the proximal end of the catheter body 502 and through a proximal opening (not shown).

Figure 24A:
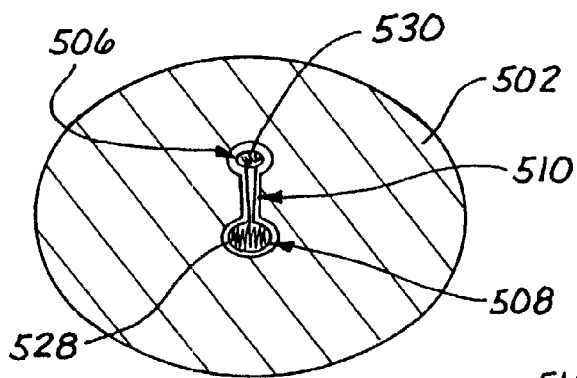
Figure 24B:
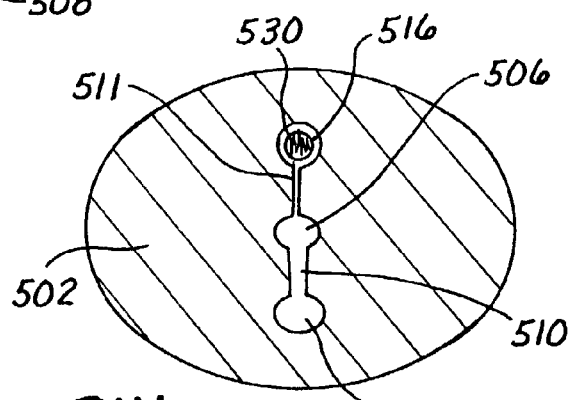

A needle outlet branch lumen 516 extends from the upper portion 506 of the main lumen 504 and through a first opening formed in the side of the catheter body 502. A needle inlet branch lumen 518 extends from the upper portion 506 of the main lumen 504 to a second opening formed in the side of the catheter 502 distal to, and preferably in alignment with, the first opening. Also, an arcuate dip AD may be formed in the portion of the main lumen 504 which passes between the needle outlet branch lumen 516 and the needle inlet branch lumen 518. Additionally, as shown in FIG. 24b, a suture passage slit 511 is formed longitudinally in the portion of the catheter body 502 located between the needle outlet branch lumen 516 and the needle inlet branch lumen 518. Such slit 511 provides a narrow suture passage channel which extends downwardly from the upper surface of the catheter body 502 into the upper portion 506 of the main lumen 504.

Figure 26:
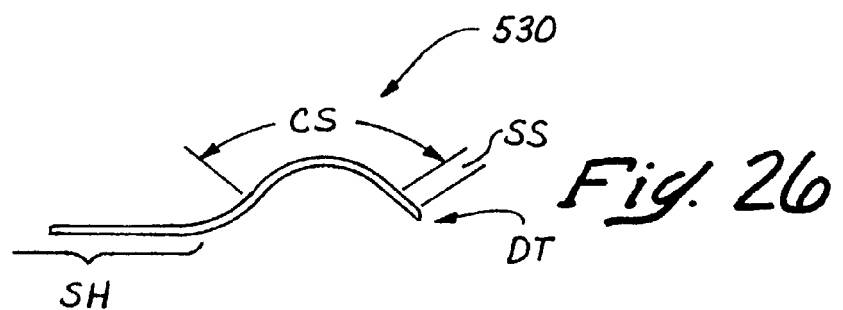
FIG. 26 is an enlarged, partial, side elevational view of the tissue penetrating member of the device of FIGS. 23–24.

A preformed resilient penetrating member, such as a curved needle 530 is slidably disposed, in a straightened configuration, within the upper portion 506 of the main lumen 504. As shown in FIG. 26, the preferred needle 530 has a straight shaft SH, a curves segment CS on the distal end of the straight shaft SH, a straight segment SS on the distal end of the curved segment CS, and a sharpened distal tip DT.

Figure 25:
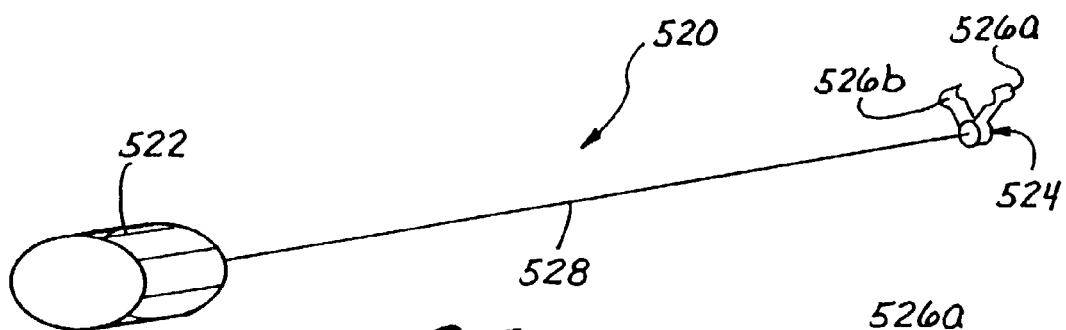
FIG. 25 is a perspective view of the needle advancing/retracting member of the device shown in FIGS. 23–24.
Figure 25A:
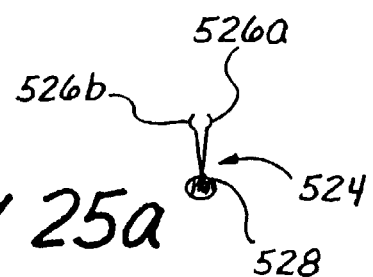
FIG. 25a is a distal end view of the needle advancing/retracting member of FIG. 25.

A needle advancing/retracting member 520 of the type shown in FIGS. 25 and 25a is slidably disposed within the catheter body 502 and is used to alternately advance and retract the needle 530, as will be described in more detail herebelow. The preferred needle advancing/retracting member 520 comprises and elongate shaft 528 having a clip 524 disposed on its distal end, and a control knob 522 on its proximal end. The control knob 522 is coupled to the clip 524 by way of a mechanical linkage (not shown) which extends through he shaft 528. The clip 524 comprises first and second laterally extending arms 526a, 526b, the ends of which are pivotally attached to a linkage hub 528. The clip resides slidably within the main lumen 504 of the catheter 502, with the hub disposed in the lower portion 508 and the arms 526a, 526b extending through the connecting channel 510 and into the upper portion 506, on either side of the needle 530, such that the needle 530 may be captured and grasped between the distal ends of the arms 526a, 526b. The shaft 528 of the needle advancing/retracting member 520 extends proximally through the lower portion 508 of the lumen and extends out of the proximal lumen opening (not shown) such that the control knob 522 is accessible to the operator during the procedure.

A length of connector material, such as suture thread 528 is connected to the proximal end of the needle 530 and extends through the proximal segment of the lower lumen portion 508, along side the shaft 528 of the needle advancing/retracting member 520.

Figure 23A:
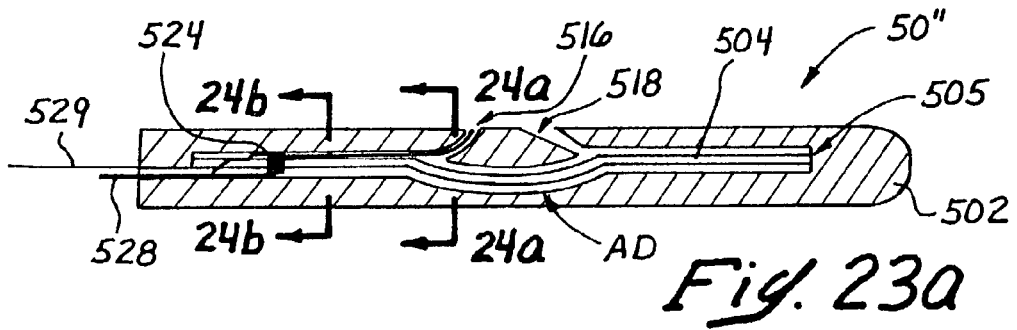

In routine operation, the catheter 502 is advanced, distal end first, through the body and the first and second openings which communicate with the needle outlet branch lumen 516 and needle inlet branch lumen 518 are positioned adjacent a first location on the wall of a luminal anatomical structure such as a blood vessel. As shown in FIG. 23a, the needle 530 is initially positioned within the upper lumen potion 506, proximal to the location at which the needle outlet branch lumen 516 diverges therefrom. Also, as shown in FIG. 23a, the needle advancing/retracting member 520 is initially positioned and deployed such that its arms 526a, 526b are grasping the needle 530 near its proximal end.

Figure 23B:
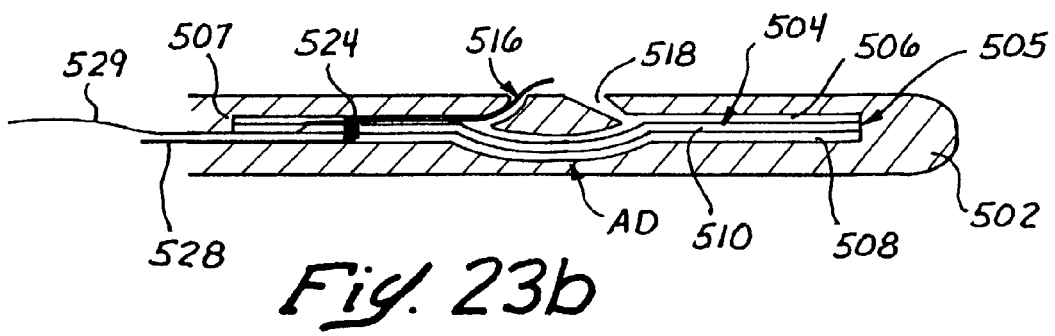

Thereafter, as shown in FIG. 23b, the needle advancing/retracting member 520 and needle 530 are advanced in the distal direction. The distal tip of the needle is configured or biased to automatically advance into the needle outlet branch lumen 516 and out of the first outlet opening as shown.

As shown in FIG. 23c, the needle advancing/retracting member 520 and needle 530 are further advanced such that the needle will penetrate fully or partially through the tissue of the wall of the luminal anatomical structure. As it advances out of the catheter 502 and through the tissue, the resilient needle 530 will assume its preformed configuration as shown in FIG. 26. This preformed shape of the needle 530 causes its distal end to reenter the catheter 502 through the needle inlet branch lumen 518, as shown in FIG. 23c. The needle inlet branch lumen 518 may be chamfered or tapered such that it is largest in diameter at the second opening in the side of the catheter and progressive narrows as it extends inwardly, thereby enhancing the ability of the distal tip DT of the needle 530 to locate and pass into the needle inlet branch lumen 518 in the manner shown.

Referring to FIG. 23d, the control knob 522 is then rotated in the direction which causes the arms 526a, 526b to pivot away from each other, thereby releasing the needle from the grip of the clip 524. As shown in FIG. 24b the communicating channel 510 of the lumen 504 is wide enough and preferably somewhat tapered, to allow the arms 526a, 526b of the clip 524 to separate sufficiently to release the needle 530 from the grip of the clip 524.

In the manner shown in FIG. 23d, the needle advancing/retracting member 520 is then advanced further in the distal direction until the clip 524 becomes positioned adjacent the distal end of the needle (e.g., at the junction of the main lumen 504 and the needle inlet branch lumen 518). The control knob 522 is then rotated in the direction which causes the arms 526a, 526b of the clip to pivot toward each other so as to capture and grasp the distal end of the needle 530 therebetween.

As shown in FIG. 23 e, the needle advancing/retracting member 520 is then further advanced in the distal direction until the clip 524 abuts against the distal end 505 of the main lumen 504 and the proximal end of the needle 530 has been pulled into the distal portion of the lumen 504 with the suture thread 529 in tow.

Thereafter, as illustrated in FIG. 23f, the control knob 522 is rotated to loosen the clip 524 and release the needle 530, and the needle advancing/retracting member 520 is retracted in the proximal direction until the clip becomes repositioned adjacent the proximal end of the needle 530.

Thereafter, as shown in FIG. 23g, the control knob 522 is rotated to tighten the clip 524 so that it once again grips the needle 530 and the needle/advancing/retracting member is then further withdrawn in the proximal direction.

As shown in FIG. 23h, the needle advancing/retracting member 520 is withdrawn in the proximal direction until the needle 530 has returned to its starting position. The suture thread 529 is concurrently pulled through the slit 511 such that the needle 530 and suture thread 529 are then prepared to repeat the above summarized steps shown in FIGS. 23a–23h.

Figure 27:
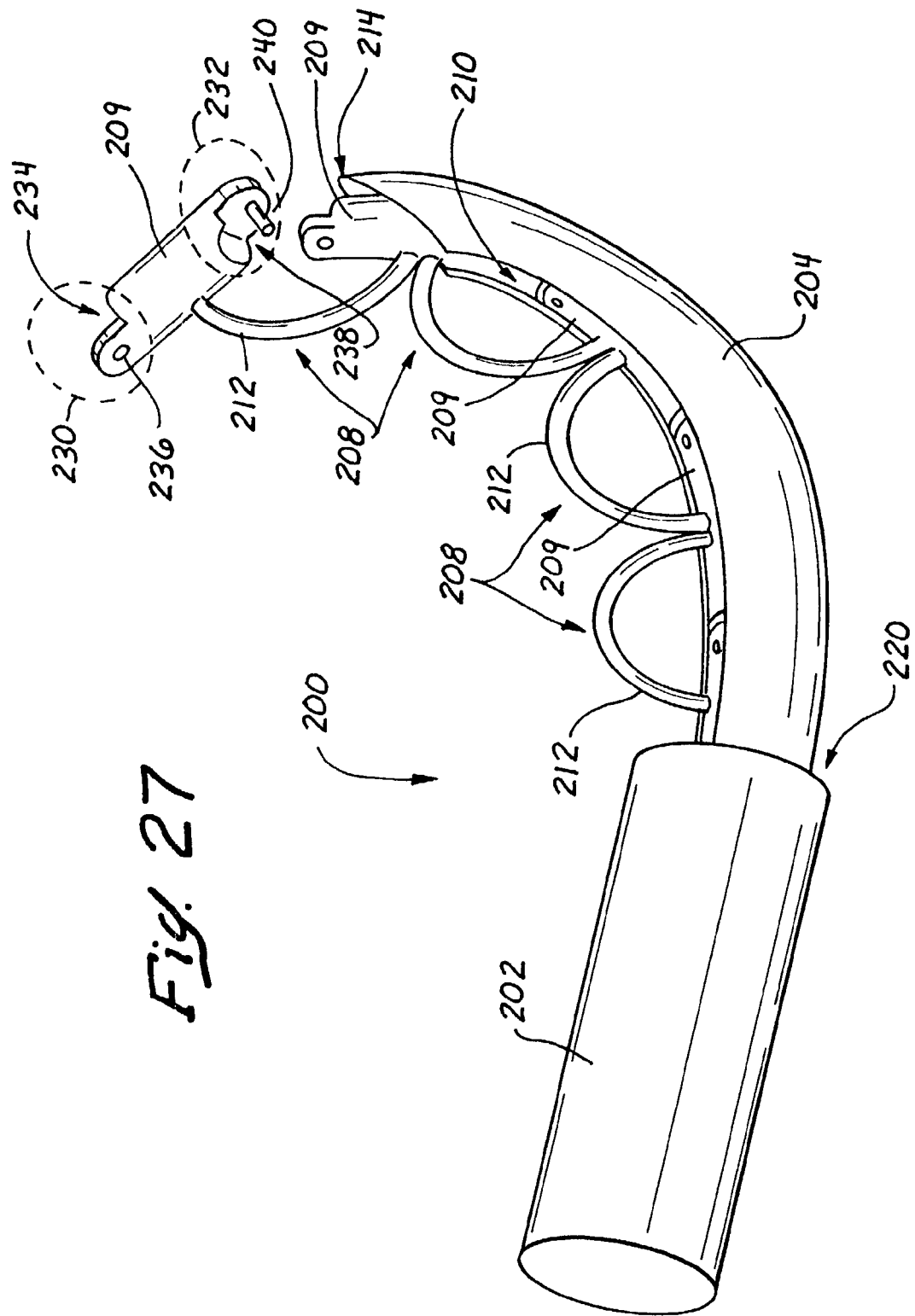
FIG. 27 is a partial perspective view of a device of the present invention for forming attachments to and or anastomoses in, the wall of a luminal anatomical structure using modified T-connector apparatus.
Figure 27A:
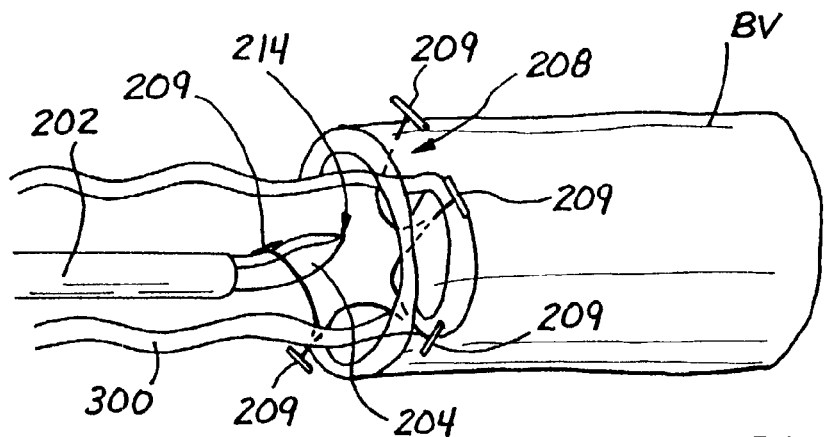
FIG. 27a is a cut-away perspective view of a segment of a blood vessel, showing the manner in which the device of FIG. 27 may be used to anchor an endoluminal graft within a blood vessel.
Figure 27B:
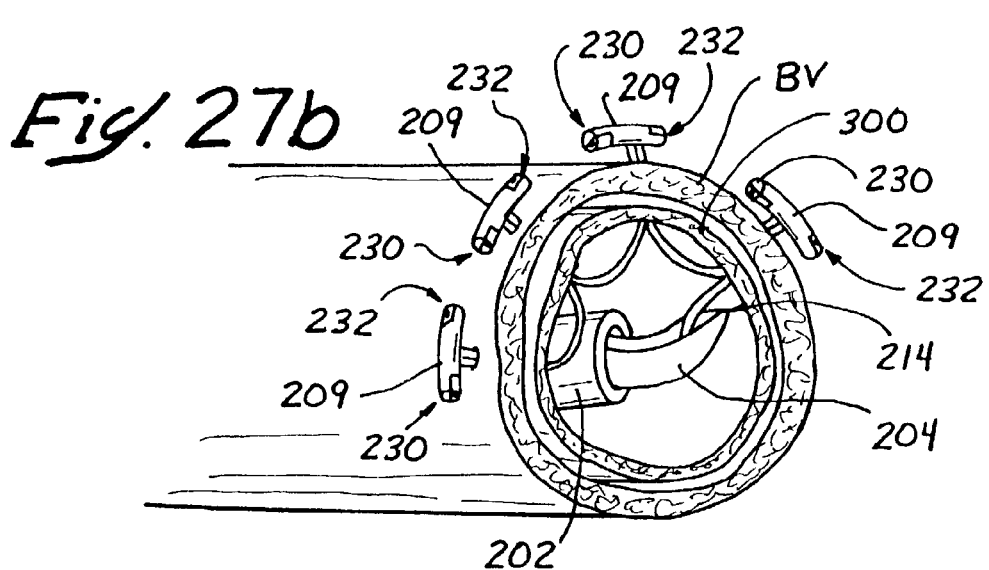
Figure 27C:
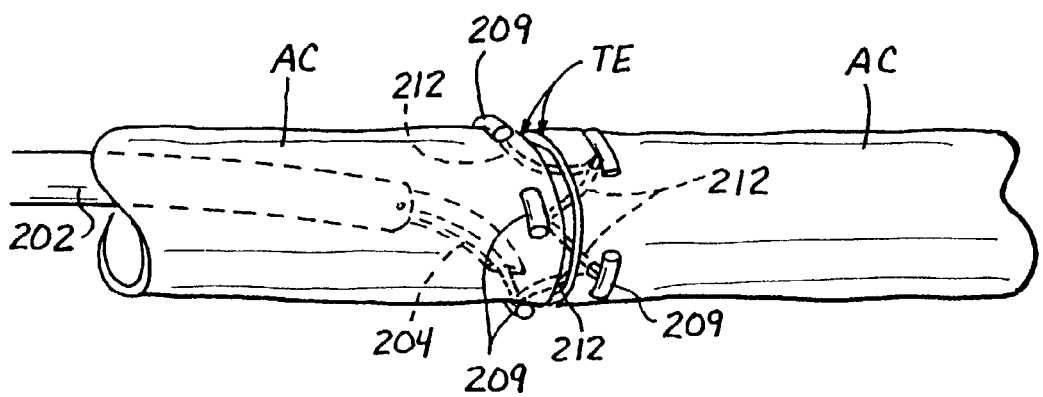
FIG. 27c is a cut-away perspective view of a tubular anatomical structure which has been transected and subsequently reconnected, by end-to-end anastomosis, using the device of FIG. 27.

The catheter may be rotationally and/or longitudinally repositioned, and the above summarized steps may be repeated, as necessary to form the desired number of stitches in the wall of the anatomical structure. One or more knots may be placed in the suture thread 629 to secure the stitch(es) using an appropriate knot-pusher device of the type known in the art and used in various endoscopic or port-access surgical procedures.

v. Fifth Embodiment—Device Useable to Form Attachments to, or Anastomoses in, a Luminal Anatomical Structure FIGS. 27–27c show another device 200 which utilizes attachment member(s) 208 having a structure similar to T-Occluder device 30 shown in FIGS. 7–11 and described hereabove. This device 200 comprises a transluminal catheter 202, which may be of rigid or pliable construction, and a slotted, hollow needle 204 which is advancable out of the catheter 202. In the particular embodiment shown, the slotted, hollow needle 204 is formed of resilient or super-elastic material, and is biased to a curved configuration, such that the distal portion of the needle 204 will assume a curved configuration as it is advanced out of a distal end opening 220 of the catheter 202. In this manner the sharpened distal tip 214 of the needle 204 will puncture fully or partially through the wall of the anatomical conduit (e.g., blood vessel) within which the distal end of the catheter 202 is positioned. It will be appreciated, however, that various other catheter/needle designs may be employed wherein the needle 204 may be deflected or otherwise caused to exit the catheter through an opening in the side of the catheter 202, rather than through the distal end thereof. The preferred needle 204 is constructed to carry a plurality of attachment members 208 and to facilitate the installation of those attachment members 208 in the wall of a luminal anatomical structure (e.g., a blood vessel). In this regard, the elongate slot 210 is preferably formed only on one side of a distal portion of the needle 204, such that the proximal shaft of the needle remains in tact and unslotted. One or more of these attachment members 208 are loaded into the lumen of the needle 204 in the manner shown in FIG. 27. Each attachment member 208 comprises a pliable link 212 formed of suture thread, a pliable filament, a strand of plastic, or other suitable material. Engagement members 209 are formed upon opposite ends of each link 212. In the particular embodiment shown, the engagement members 209 are in the nature of cross members, each such cross member having a longitudinal axis LA-T which is substantially perpendicular to the longitudinal axis LA-L of the link 212. In some embodiments, the engagement members will be coupled to one another in a chain-like fashion, while they remain loaded in the lumen of the needle 204, but each such engagement member 209 will become uncoupled from its neighboring engagement member 209 when it is expelled out of the distal tip 214 of the needle 204. With respect to the particular cross member-type engagement members 209 shown in FIGS. 23–23c, each such engagement member 209 has a first connector 230 formed on one end thereof, and a second connector 232 formed on the other end thereof. The first connector 230 of one engagement member 209 is connected to, but disconnectable from, the second connector 232 of a neighboring engagement member 209 within the lumen of the needle 204. This chaining or linking of the engagement members 209 allows them to be moved longitudinally in unison so long as they are sequentially packed in the lumen of the needle 204. However, when one engagement member 209 is expelled from the needle 204 and caused to assume an orientation which is non-coaxial to and/or not in end-to-end alignment with its neighboring engagement member 209, the second connector 232 of that engagement member 209 will disconnect and separate from the first connector 230 of the neighboring engagement member 209. In this manner the next neighboring engagement member 209 remains within the lumen of the needle 204, and remains coupled to any subsequent engagement members 209 which are also within the needle lumen, as illustrated in FIG. 23. The connectors 230, 232 formed on the engagement members 209 may be constructed and configured in many suitable ways, and may create various types of suitable interconnections (e.g., mechanical, frictional, adhesive, magnetic, etc.). In the particular embodiment shown, the first connector 230 of each engagement member 209 comprises a first notch 234 having a receiving aperture 236 associated therewith, and the second connector 232 of each engagement member 209 comprises a second notch 238 having a raised projection 240 (e.g., a lug, post, tongue, boss, etc.) associated therewith. The second connector 232 of one engagement member 209 is received within the receiving aperture 236 of the first connector 230 of the neighboring engagement member 209, so as to couple or link those engagement members 209, while they remain in sequential, contiguous alignment within the lumen of the needle 204. The links 212 of these interconnected attachment members 208 protrude, in looped fashion, out of the slot 210 of the needle 204, as shown. An ejector/retraction member (not shown) is passed through the lumen of the needle 204, proximal to the proximal-most engagement member 209 loaded into the lumen of the needle. Such ejector/retraction member is connected to or grasps the proximal-most engagement member, and is useable to selectively expel one engagement member 209 at a time from the distal tip 214 of the needle 204. In operation, the catheter 202 is inserted and advanced transluminally until the distal end of the catheter 202 is positioned in the lumen of a luminal anatomical structure, at the location where an anastomosis or attachment is to made. The needle 204 is then advanced out of the distal end aperture 220 of the catheter 202 until the sharpened distal tip 214 of the needle has punctured fully or partially through the wall of the luminal anatomical structure. Thereafter, the ejection/retractor member (not shown) is advanced in the distal direction to expel the first (i.e., distal-most) one of the engagement members 209 out of the end of the needle 204. As the first engagement member 209 passes out of the end of the needle 204 the force exerted by its link 212 will cause that engagement member 209 to assume an orientation which causes its second connector 323 to become uncoupled from the first connector 230 of the next engagement member 209. The ejection/retractor member may then be retracted in the proximal direction to pull any protruding portion of the next engagement member 209 back into the lumen of the needle 204. In this manner, the first expelled engagement member 209 is deployed outside of the luminal anatomical structure such that it will abut against or engage the outer surface of the luminal anatomical structure (e.g., the adventitial surface or layer of a blood vessel) as illustrated in FIGS. 23a, b and c. The needle 204 is then retracted into the catheter 202, and the catheter 202 is repositioned (i.e., moved longitudinally and/or rotated) such that the needle 204 becomes aimed at a second location on the wall of the luminal anatomical structure. The needle is then readvanced through the wall of the luminal anatomical structure and the above-described procedure repeated to place the second engagement member 209 at a second location outside of the luminal anatomical structure, with the link 212 which joins those two engagement members 209 traversing through the lumen of the anatomical structure. This entire procedure may then be repeated one or more times until the desired suture line or row(s) of attachment members 208 have been installed to form the desired attachment or anastomosis. In at least some applications, the engagement members 209 will be initially loaded into the lumen of the needle 204 in a chain like fashion and all of the engagement members 209, except for those on either end of the chain, will have two (2) links connected thereto, as shown in the figures. This will cause the engagement members to form a continuous suture line, attachment or anastomosis in the wall of the luminal anatomical structure. 30 This device 200 may be used for many purposes, including a.) attaching or anchoring an endoluminal graft, stent or other item/apparatus to the luminal anatomical structure, b.) connecting the luminal anatomical structure to another anatomical structure, or c.) forming an anastomotic junction between the luminal anatomical structures and another anatomical structure or between two approximated cut ends of the same luminal anatomical structure (as may occur following transection or resection of that luminal anatomical structure). FIGS. 23a and 23b specifically illustrate one way in which this device may be used to anchor the end(s) of a tubular endoluminal graft 300 to the wall of a blood vessel BV. As shown in FIGS. 27a and 27b, the tubular graft 300 is placed within the lumen of the blood vessel BV at a desired location (e.g., such that it extends through an aneurysmic, diseased or injured portion of that blood vessel BV). The catheter 202 is then advanced into the luminal anatomical structure and positioned such that the outlet opening 220 at the distal end of the catheter is adjacent one end of the graft 300. A series of the attachment members 208 are then installed, in an annular array, to anchor that end of the graft 300 to the wall of the blood vessel BV. The same procedure may then be repeated to anchor the other end of the tube graft 300 as well. In this manner, the graft 300 is firmly held in place and prevented from migrating within the blood vessel. In applications wherein it is desired to have the end(s) of the graft 300 held tightly against the wall of the blood vessel BV to prevent blood from seeping into or entering the space between the outer surface of the graft and the wall of the blood vessel (e.g., an "endoleak"), the links 212 of the attachment members 208 may be formed of elastic material to accomplis such tight approximation of the graft, or the links 212 may be formed of malleable material and twisted or deformed to a shortened configuration to pull the graft tightly against the blood vessel wall. Alternatively a sealing substance (e.g., a biologically compatible adhesive) or space-occupying members (e.g., embolization coils, beads, gelfoam, etc.) may be applied or deposited about the end(s) of the graft 300 to prevent such leakage of blood around the graft.

FIG. 27c shows another possible application wherein the device 200 is used to form an end to end anastomosis between transected ends TE of an anatomical conduit AC such as a blood vessel, duct, tube or passageway of the body. In this application, the engagement members 209 are installed in a staggered radial array (i.e. a zig-zag array around the anastomotic junction) so as to connect the transected ends TE of the anatomical conduit AC in abutting approximation and the desired alignment. Such staggered positioning of the engagement members 209 may be accomplished by longitudinally advancing and retracting the catheter, back and forth, in conjunction with each incremental rotation thereof, to cause the engagement members 209 to be installed around, and on opposite sides of, the anastomotic junction, as shown in FIG. 27c.

Figure 27D:
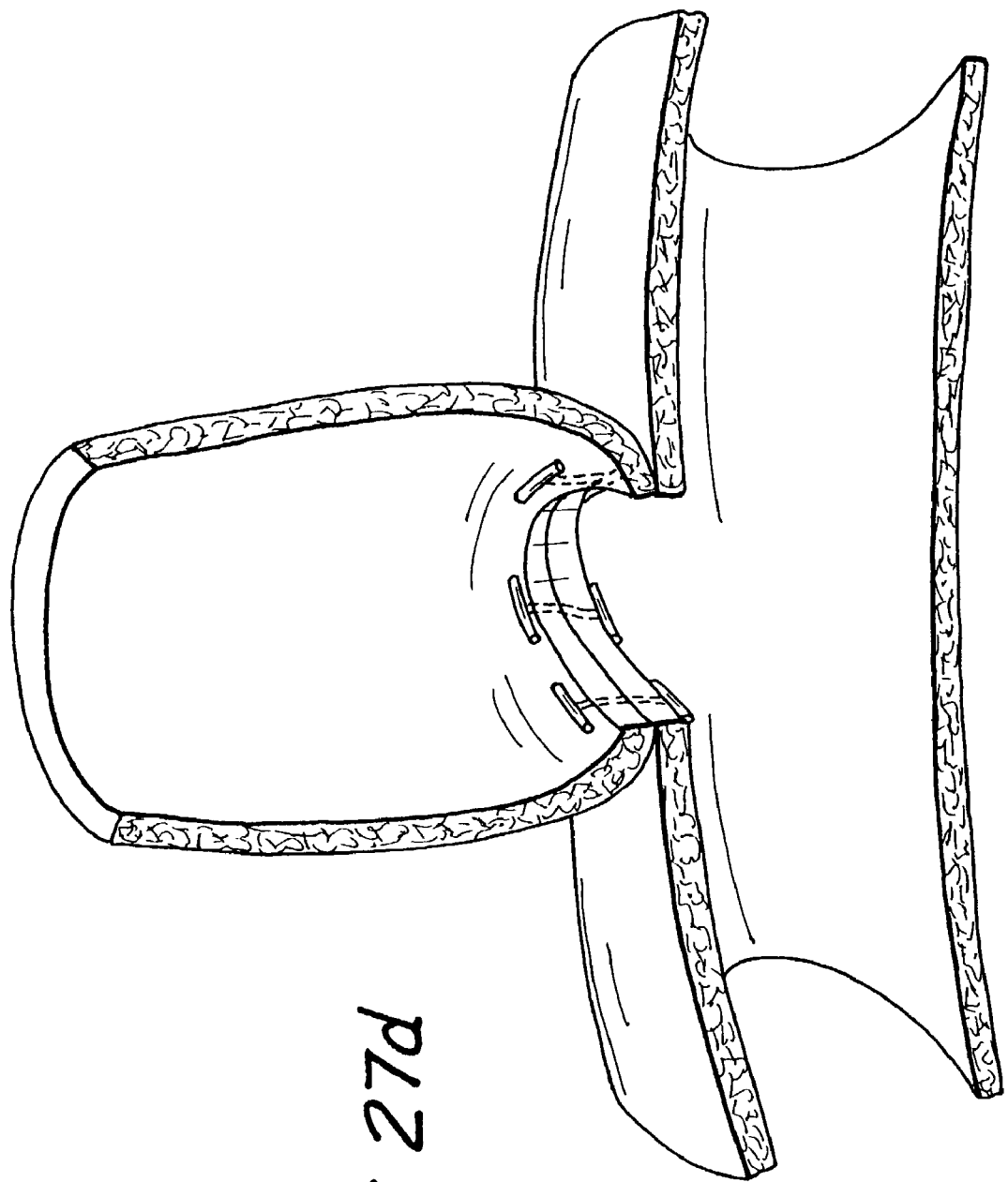
FIG. 27d is a perspective view of two (2) tubular anatomical conduits which have been prepared and approximated in end-to-side fashion, and which have been anastomosed by way of interrupted connector bars which are a variation of the device shown in FIG. 27.
Figure 28A:
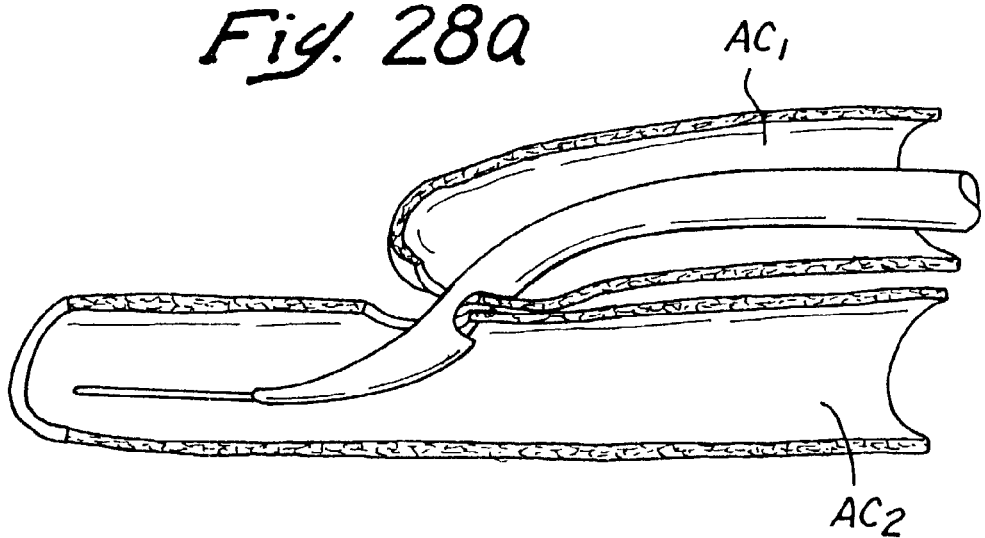
FIG. 28a is a longitudinal sectional view of two (2) anatomical conduits being connected by end-to-side anastomosis using an intraluminal device of the present invention.
Figure 28B:
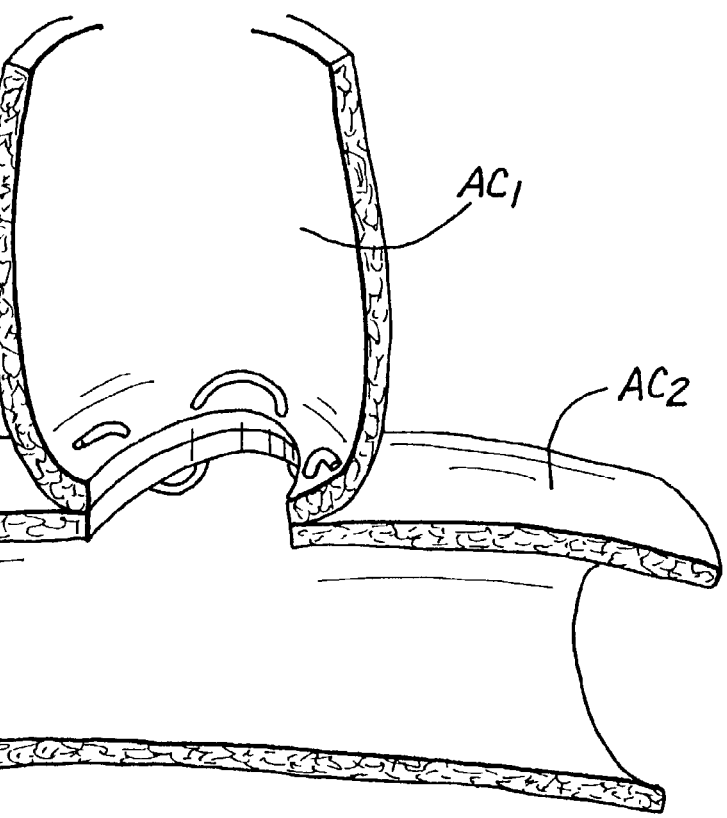
FIG. 28b is a longitudinal sectional view of the two (2) anatomical conduits of FIG. 28a, after undergoing end-to-side anastomosis by an intraluminal device of the present invention.
Figure 29A:
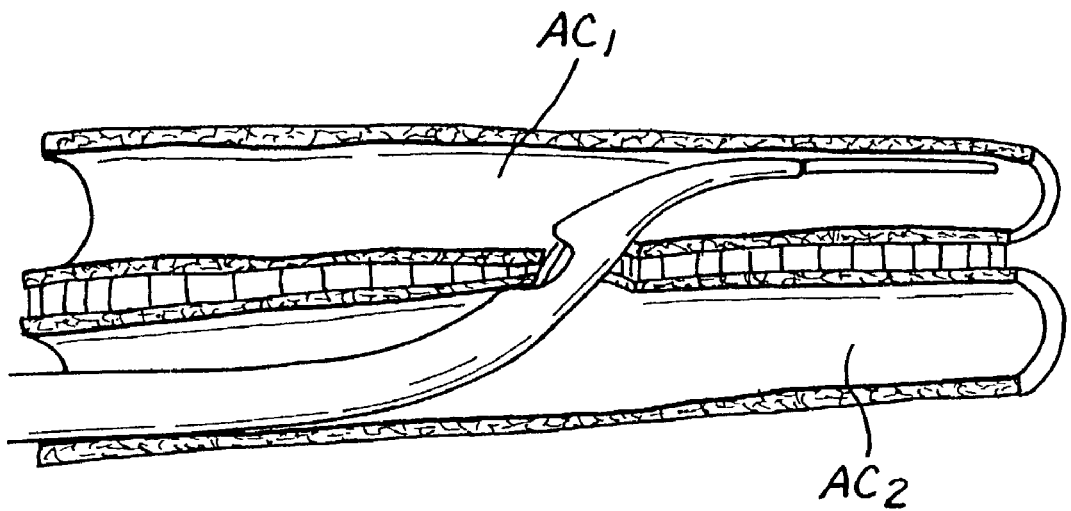
FIG. 29a is a longitudinal sectional view of two (2) anatomical conduits being connected by side-to-side anastomosis using an intraluminal device of the present invention.
Figure 29B:
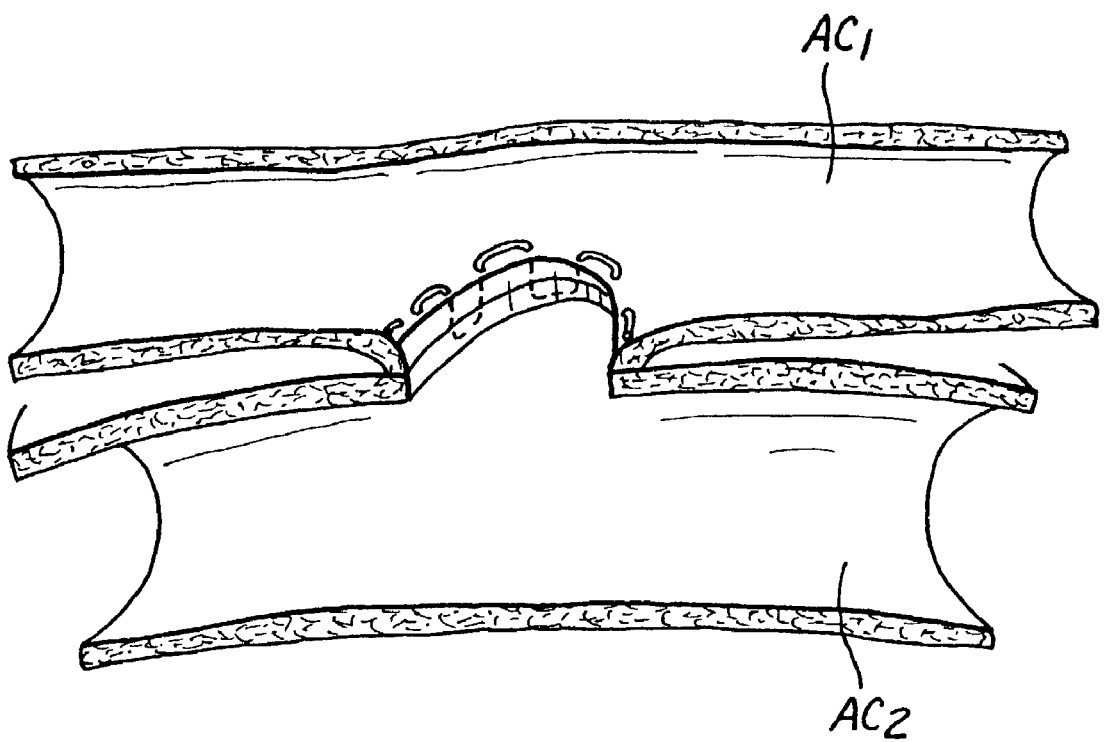
FIG. 29b is a longitudinal sectional view of the two (2) anatomical conduits of FIG. 29a, after undergoing side-to-side anastomosis by an intraluminal device of the present invention.

FIG. 27d shows another possible application wherein a device similar to that shown in FIG. 27 has been used to install a series of interrupted attachment members 208' to form an end-to-side anastomosis between two anatomical conduits. These interrupted attachmentrr members 208' differ from the continuous attachment members 208 shown in FIGS. 27–27c in a single link portion 212' is connected to each engagement member 209', rather than having some engagement members 209 which have two link portions 212 of adjacent attachment apparatus 209 both connected thereto. Those skilled in the art will understand that, in this manner, these attachment apparatus 208' are installed in an interrupted rather than continuous fashion.

Those skilled int he art will further understand and appreciate that the devices 5, 50', 50", 50'" and 200 which have been disclosed hereabove as being useable to form anastomotic junctions between two (2) anatomical conduits or two (2) segments of the same anatomical conduit, may be used to form numerous types of anastomotic junctions, and will not be limited to only the end-to-end type junctions specifically shown in FIG. 18 or 27c. Rather, these devices 50, 50', 50'', 50''' or 200 may additionally be used to form end-to-side junctions as illustrated schematically in FIGS. 28a & 28b, and/or side-to-side junctions as illustrated schematically in FIGS. 29a & 29b.

It is to be further appreciated and understood that the invention as been described hereabove with reference to certain presently preferred embodiments or examples only, and no attempt has been made to exhaustively describe all possible embodiments or examples in which the invention may be practiced, or take physical form. Indeed, various additions, deletions, modifications, and alterations may be made to the above-described embodiments and examples without departing from the intended spirit and scope of the invention. Accordingly, it is intended that all such additions, deletions, modifications, and alterations be included within the scope of the following claims.

What is claimed is:

1. A method for forming an attachment to, or anastomosis in, the wall of the anatomical structure by placing at least one attachment apparatus in the wall if the anatomical structure, said method comprising the steps of:
   A. providing an intraluminal device which comprises:
      i.) an elongate catheter which is insertable into the lumen of the anatomical structure;
      ii.) an elongate tissue-penetrating member initially disposed within said catheter, said tissue-penetrating member being subsequently advancable from the catheter and at least partially through the wall of the anatomical structure into which said catheter has been advanced, said tissue-penetrating member having a lumen which extends longitudinally through at least a distal portion of the tissue-penetrating member, and an outlet opening formed in the distal end of the tissue-penetrating member in communication with said lumen; and,
      iii.) at least one attachment apparatus comprising an elongate, flexible link having at least first and second engagement members associated with opposite ends thereof, said attachment apparatus including both of said first and second engagement members being initially loaded into the lumen of the tissue penetrating member and incrementally advancable out of the outlet opening in the distal end of the tissue-penetrating member such that the first engagement member may be expelled from the lumen of the tissue penetrating member at a first location and the second engagement member may be expelled from the lumen of the tissue penetrating member at a second location and said link(s) will extend therebetween to form the desired attachment or anastomosis;
   B. positioning the catheter within the lumen of the anatomical structure;
   C. advancing the tissue penetrating member out of the catheter a first time such that the sharpened distal tip of the tissue penetrating member penetrates at least partially through the wall of the anatomical structure and the outlet opening of the needle becomes situated adjacent said first location;
   D. expelling the first engagement member out of the lumen of the tissue penetrating member through the outlet opening in the distal end of the tissue penetrating member such that said first engagement member will engage the wall of the luminal anatomical structure at said first location;
   E. retracting the tissue penetrating member into the catheter;
   F. repositioning the catheter within the lumen of the anatomical structure;
   G. advancing the tissue penetrating member from the catheter a second time, such that the sharpened distal tip of the tissue penetrating member penetrates at least partially through the anatomical structure and the outlet opening becomes situated adjacent said second location;
   H. expelling the second engagement member out of the lumen of the tissue penetrating member through the outlet opening in the distal end of the tissue penetrating member such that the second engagement member will engage the wall of the anatomical structure at said second location, and the link portion of said attachment apparatus extends between said first location and said second location.

2. The method of claim 1 wherein the method is performed to attach an article to the wall of the anatomical structure, and wherein the method further comprises the step of:
   positioning the article at a desired location adjacent the wall of the anatomical structure, and wherein the catheter-positioning of step B is performed such that the tissue-penetrating member will pass through a portion of the article as well as through the tissue of the anatomical structure wall.

3. The method of claim 1 wherein said method is performed for the purpose of forming an anastomotic junction between two segments of said anatomical structure, and wherein said method further comprises the step of:
   approximating the two segments of said anatomical structure and causing the first and second locations to be positioned such that the attachment apparatus will form an anastomosis between the approximated segments of said anatomical structure.

4. The method of claim 1 wherein the first and second engagement members are serially loaded in the lumen of the tissue penetrating member before performance of Step D.

5. The method of claim 4 wherein the first and second engagement members are coupled together while they remain loaded in the lumen of the lumen of the tissue penetrating member and wherein Step D further comprises uncoupling the first engagement member from the second engagement member.

6. The method of claim 1 wherein the anatomical structure comprises a blood vessel.

7. The method of claim 6 wherein at least one of Steps C and G comprises advancing the tissue penetrating member outwardly through the wall of the blood vessel and wherein at least one of Steps D and H comprises expelling the engagement member such that it engages an adventitial surface of the blood vessel.

8. The method of claim 1 wherein said method is performed for the purpose of connecting a first anatomical structure and a second anatomical structure, and wherein said method further comprises the step of:
   approximating the first and second anatomical structures and causing the first and second locations to be positioned such that the attachment apparatus will anastomose the first anatomical structure to the second anatomical structure.

9. The method of claim 1 wherein the method is carried out to form an end to end anastomosis between two luminal anatomical structures or between transected ends of the same luminal anatomical structure.

* * * * *